US012109409B2

(12) United States Patent
Park et al.

(10) Patent No.: US 12,109,409 B2
(45) Date of Patent: Oct. 8, 2024

(54) MICRO PROBE ARRAY DEVICE AND MANUFACTURING METHOD OF THE DEVICE

(71) Applicant: Industry-Academic Cooperation Foundation, Dankook University, Gyeonggi-do (KR)

(72) Inventors: Jae-Hyoung Park, Gyeonggi-do (KR); Seung-Ki Lee, Seoul (KR); Donggen Choi, Gyeonggi-do (KR); So-Bin Shin, Gyeonggi-do (KR); Ji-Yeon Kim, Gyeonggi-do (KR)

(73) Assignee: Industry-Academic Cooperation Foundation, Dankook University, Gyeonggi-do (KR)

( * ) Notice: Subject to any disclaimer, the term of this patent is extended or adjusted under 35 U.S.C. 154(b) by 1070 days.

(21) Appl. No.: 17/012,304

(22) Filed: Sep. 4, 2020

(65) Prior Publication Data

US 2021/0311092 A1 Oct. 7, 2021

(30) Foreign Application Priority Data

Apr. 1, 2020 (KR) .................. 10-2020-0039689
Apr. 1, 2020 (KR) .................. 10-2020-0039699
(Continued)

(51) Int. Cl.
*A61N 1/04* (2006.01)
*A61N 1/05* (2006.01)
(Continued)

(52) U.S. Cl.
CPC ......... *A61N 1/0543* (2013.01); *A61N 1/0476* (2013.01); *G01N 27/30* (2013.01);
(Continued)

(58) Field of Classification Search
CPC ................ A61N 1/0543; A61N 1/0476; A61N 1/36046; G01N 27/30; G01Q 70/06;
(Continued)

(56) References Cited

U.S. PATENT DOCUMENTS

2007/0276211 A1   11/2007   Mir et al.
2018/0271414 A1*  9/2018   Deck .................. H01R 13/625
(Continued)

FOREIGN PATENT DOCUMENTS

JP       2008-188123 A      8/2008
KR   10-2007-0112760 A     11/2007
(Continued)

OTHER PUBLICATIONS

Byun, D. "Fabrication of a flexible penetrating microelectrode array for use on curved surfaces of neural tissues", Journal of Micromechanics and Microengineering, vol. 23, No. 12 (Oct. 30, 2013) 125010 (14 pages).

*Primary Examiner* — Ankit D Tejani
*Assistant Examiner* — Joshua Brendon Solomon
(74) *Attorney, Agent, or Firm* — JCIPRNET

(57) ABSTRACT

A micro probe array device and method of manufacturing are disclosed. In the micro probe array device, a plurality of working electrodes are arranged in an array form, so that an individual electric signal can be applied to an object for each working electrode. In the micro probe array device, the height of the working electrode may be different, the working electrode and the counter electrode may constitute a double electrode, or the substrate may be made of a flexible material.

35 Claims, 17 Drawing Sheets

(30) Foreign Application Priority Data

| | | | |
|---|---|---|---|
| Jun. 8, 2020 | (KR) | ........................ | 10-2020-0068984 |
| Sep. 4, 2020 | (KR) | ........................ | 10-2020-0112718 |
| Sep. 4, 2020 | (KR) | ........................ | 10-2020-0112720 |
| Sep. 4, 2020 | (KR) | ........................ | 10-2020-0112723 |

(51) Int. Cl.
*G01N 27/30* (2006.01)
*G01Q 70/06* (2010.01)
*G01Q 70/16* (2010.01)

(52) U.S. Cl.
CPC ............. *G01Q 70/06* (2013.01); *G01Q 70/16* (2013.01); *A61B 2562/046* (2013.01); *A61B 2562/125* (2013.01)

(58) Field of Classification Search
CPC .............. G01Q 70/16; A61B 2562/046; A61B 2562/125; A61B 2562/0209
See application file for complete search history.

(56) References Cited

U.S. PATENT DOCUMENTS

| | | | | |
|---|---|---|---|---|
| 2019/0021619 | A1* | 1/2019 | Dayeh | ................... B82Y 15/00 |
| 2021/0204878 | A1* | 7/2021 | Huang | ................. A61B 5/1473 |
| 2021/0310979 | A1* | 10/2021 | Gandolfo | ........... G01N 33/4836 |
| 2023/0053962 | A1* | 2/2023 | Kendall | ............. G01N 33/6887 |

FOREIGN PATENT DOCUMENTS

| | | | | |
|---|---|---|---|---|
| KR | 10-1241340 B1 | 10/2012 | | |
| KR | 10-1376012 B1 | 6/2013 | | |
| KR | 10-2013-0091917 A | 8/2013 | | |
| KR | 10-1618923 B1 | 11/2014 | | |
| KR | 10-2015-0071233 A | 6/2015 | | |
| KR | 10-1610441 B1 | 6/2015 | | |
| KR | 101616294 B1 | 4/2016 | | |
| KR | 10-2016-0123951 A | 10/2016 | | |
| KR | 10-1865446 B1 | 10/2016 | | |
| KR | 10-1847745 B1 | 4/2018 | | |
| KR | 10-1962011 B1 | 10/2018 | | |
| KR | 10-1978600 B1 | 5/2019 | | |
| WO | WO-2020035570 A1 * | 2/2020 | ................ A61B 5/24 | |
| WO | 2020069565 A1 | 4/2020 | | |
| WO | WO-2021062475 A1 * | 4/2021 | ........... A61B 5/1451 | |

* cited by examiner

STEP 7

STEP 8

STEP 9

STEP 10

STEP 11

STEP 12

STEP 13

STEP 14

STEP 15

STEP 16

STEP 17

STEP 18

STEP 13

STEP 14

- Silicon
- PDMS
- Al
- Silicon Oxide
- Parylene
- Cr/Au

MICRO PROBE ARRAY DEVICE AND MANUFACTURING METHOD OF THE DEVICE

CROSS-REFERENCE TO RELATED APPLICATION(S)

This application claims the priority benefit of Korean Patent Application No. 10-2020-0039689 filed on Apr. 1, 2020, Korean Patent Application No. 10-2020-0039699 filed on Apr. 1, 2020, Korean Patent Application No. 10-2020-0068984 filed on Jun. 8, 2020, Korean Patent Application No. 10-2020-0112718 filed on Sep. 4, 2020, Korean Patent Application No. 10-2020-0112720 filed on September 04, and Korean Patent Application No. 10-2020-0112723 filed on Sep. 4, 2020, in the Korean Intellectual Property Office, the disclosures of which are incorporated herein by reference for all purposes.

BACKGROUND

1. Field of the Invention

The following descriptions relate to a micro probe array device and a manufacturing method.

2. Description of the Related Art

When a disease occurs in a specific tissue of the human body, it is possible to treat the disease by providing electrical stimulation to an area where the disease has occurred in the tissue. In this case, a device composed of a plurality of electrodes was used to provide electrical stimulation to a specific tissue.

However, when the interference between the plurality of electrodes is high, there is a problem that the spatial resolution is not high then the treatment effect is low. And certain tissues have a curvature in an irregular shape. Therefore, the device needs to be implanted so that the electrode is inserted into the tissue at a certain depth while being in close contact with the tissue according to the curvature of the tissue. In addition, it is also necessary to apply a separate electrical signal to each of the plurality of electrodes to apply stimulation to a local area in the tissue.

SUMMARY

An aspect provides a micro probe array device and a manufacturing method of the micro probe array device.

According to an aspect, there is provided a micro probe array device including a substrate; a via contact formed through the substrate; a working electrode in the form of a probe formed on an upper end of the via contact: a reference electrode formed at a lower end of the via contact and is configured to provide an electric signal to the working electrode; an insulating layer formed on a portion of the working electrode, wherein the working electrode is arranged in an array form, and at least one working electrode having different heights is included in the micro probe array device.

A tip region of the working electrode is not covered by the insulating layer and is exposed to the outside, and a remain area except for the tip area of the working electrode is covered by an insulating layer.

The height of the working electrode is set differently according to the distance between the substrate and the objects contacting the tip region of the working electrode, wherein the distance is determined according to the shape or curvature of the object.

The working electrode is connected to the reference electrode through a via contact, and wherein the via contacts are spaced apart from each other according to a predetermined distance in the substrate and are disposed independently of each other in the substrate.

The tip region of the working electrode is configured to contact with the object and provide an electric signal transmitted through the via contact to the object or to obtain an electric signal transmitted from the object.

The height of the working electrode is adjusted corresponding to the curvature of the object.

The micro probe array device further includes a counter electrode is separated from a working electrode due to the insulating layer, and wherein a flow of electricity signal flow is formed with the working electrode in contact with an object.

A distance between the working electrode and the object becomes closer or a depth to be inserted into the object increases, when a mechanical pressure of an actuator is applied to the reference electrode.

The mechanical pressure is determined based on the electrical signal being fed back from the object.

The mechanical pressure increases, when the electric signal fed back from the object is less than or equal to a predetermined strength.

The substrate is formed of a fixed material that is not deformed by external pressure or a flexible material that is deformed by external pressure.

According to another aspect, there is provided a manufacturing method of the micro probe array device, comprising: (1) a process of forming a plurality of cylinders in an array form; (2) a process of anodic bonding a silicon wafer and a glass wafer; (3) a process of reflowing the silicon-etched area with glass; (4) a process of removing a glass wafer present on a upper portion of the silicon wafer through chemical/mechanical polishing (CMP); (5) a process of patterning a silicon oxide and a photoresist on a front surface of the silicon wafer, which is the opposite side of a rear surface of the silicon wafer filled with the glass wafer; (6) a process of performing a first anisotropic etching on the front surface of the silicon wafer patterned with silicon oxide and photoresist in the silicon wafer; (7) a process of removing the photoresist and performing a second anisotropic etching; (8) a step of removing the silicon oxide layer with a hydrofluoric acid solution and performing silicon isotropic wet etching; (9) a process of patterning a photoresist on a micro probe area according to photolithography and depositing a conductive material; (10) a process of removing the photoresist from the micro probe area and lifting-off so that only the conductive material deposited on the micro probe area remains; (11) a process of depositing an insulating material in the micro probe region; (12) a process of spin coating a photoresist on the micro probe area; (13) a process of etching the photoresist through a self-alignment process and depositing a conductive material on the rear surface of the glass wafer; (14) a process of patterning a photoresist on the conductive material deposited on the rear surface of the glass wafer; (15) a process of etching the conductive material; (16) a process of dicing to remove the silicon at the edge so that the micro probe array device can be implanted on the object.

According to another aspect, there is provided a micro probe array device including a substrate; a via contact formed through the substrate; a working electrode in the form of a probe formed on an upper end of the via contact: a reference electrode formed at a lower end of the via contact and is configured to provide an electric signal to the working electrode: a first insulating layer formed on the working electrode: a counter electrode formed on the first insulating layer; a second insulating layer formed on the counter electrode, wherein a flow of the electrical signal between the working electrode, the counter electrode, and objects in contact with the working electrode.

A tip region of the working electrode is not covered by the insulating layer and is exposed to the outside, and a remain area except for the tip area of the working electrode is covered by an insulating layer.

The working electrode and the counter electrode are separated by a first insulating layer.

A length of the working electrode is different from a length of the counter electrode.

The length of the working electrode is longer than the length of the counter electrode.

The height of the working electrode is set differently according to the distance between the substrate and the objects contacting the tip region of the working electrode, wherein the distance is determined according to the shape or curvature of the object.

The working electrode is connected to the reference electrode through a via contact, and wherein the via contacts are spaced apart from each other according to a predetermined distance in the substrate and are disposed independently of each other in the substrate.

The tip region of the working electrode is configured to contact with the object and provide an electric signal transmitted through the via contact to the object or to obtain an electric signal transmitted from the object.

The height of the working electrode is adjusted corresponding to the curvature of the object.

A distance between the working electrode and the object becomes closer or a depth to be inserted into the object increases, when a mechanical pressure of an actuator is applied to the reference electrode.

The mechanical pressure is determined based on the electrical signal being fed back from the object.

The mechanical pressure increases, when the electric signal fed back from the object is less than or equal to a predetermined strength.

A specific region of the counter electrode is not covered by the second insulating layer and is exposed to the outside, and a remain area except for the specific area of the counter electrode is covered by an insulating layer.

A partial region of the counter electrode is covered by a second insulating layer, and the remaining regions except for the partial region are exposed without being covered by the second insulating layer.

The working electrodes that are adjacent to each other are formed to be spaced apart from each other, and wherein the counter electrodes that are adjacent to each other are formed to be connected to each other or formed to be spaced apart from each other.

The substrate is formed of a fixed material that is not deformed by external pressure or a flexible material that is deformed by external pressure.

According to another aspect, there is provided a manufacturing method of the micro probe array device including (1) a process of anisotropic etching of a rear surface of a silicon wafer for individual addressing of the micro probe; (2) a process of anodic bonding the silicon wafer and the glass wafer to insulate the micro probe, and reflowing the glass wafer; (3) a process of removing a glass existing on the silicon wafer through chemical/mechanical polishing (CMP) and reducing thickness of the silicon wafer by a predetermined size; (4) a process of depositing a silicon oxide layer and patterning to make a silicon cylinder to be a micro probe; (5) a process of anisotropic etching process to create the silicon cylinder to be the micro probe; (6) a process of removing a photoresist and forming the micro probe having a sharp tip area through wet etching; (7) a process of depositing a photoresist and patterning according to photolithography so that a working electrode remains on the micro probe; (8) a process of depositing a conductive material for forming the working electrode; (9) a process of a lift-off process to remove the photoresist from the micro probe region and remain only the conductive material deposited on the micro probe; (10) a process of depositing an insulating material and a conductive material for forming a counter electrode and then depositing the insulating material again; (11) a process of spin coating a photoresist; (12) a process of etching a second deposited parylene through a self-alignment process, and then removing the spin-coated photoresist; (13) a process of spin coating a photoresist; (14) a process of etching the second deposited conductive material through a self-alignment process and removing the spin-coated photoresist; (15) a process of spin coating a photoresist; (16) a process of depositing a conductive material on the rear surface of the silicon wafer and depositing a photoresist; (17) a process of etching the conductive material deposited on the rear surface of the silicon wafer and removing the photoresist.

According to another aspect, there is provided a micro probe array device including a substrate: a via contact formed through the substrate; a working electrode in the form of a probe formed on an upper end of the via contact: a reference electrode formed at a lower end of the via contact and is configured to provide an electric signal to the working electrode; an insulating layer formed on a portion of the working electrode, wherein the substrate is composed of a flexible material that can be bent by external pressure to correspond to the curvature of an object.

A tip region of the working electrode is not covered by the insulating layer and is exposed to the outside, and a remain area except for the tip area of the working electrode is covered by an insulating layer.

The height of the working electrode is set differently according to the distance between the substrate and the objects contacting the tip region of the working electrode, wherein the distance is determined according to the shape or curvature of the object.

The working electrode is connected to the reference electrode through a via contact, and wherein the via contacts are spaced apart from each other according to a predetermined distance in the substrate and are disposed independently of each other in the substrate.

A flexible PCB is coupled to the lower end of the micro probe array device, wherein a hole of the flexible PCB is formed at a position of a reference electrode of the micro probe array device and is coupled to the micro probe array device through a conductive epoxy.

The tip region of the working electrode is configured to contact with the object and provide an electric signal transmitted through the via contact to the object or to obtain an electric signal transmitted from the object.

The height of the working electrode is adjusted corresponding to the curvature of the object.

A counter electrode is disposed on the insulating layer, wherein a flow of electric signal between the working electrode and the counter electrode is formed.

A distance between the working electrode and the object becomes closer or a depth to be inserted into the object increases, when a mechanical pressure of an actuator is applied to the reference electrode.

The mechanical pressure is determined based on the electrical signal being fed back from the object.

The mechanical pressure increases, when the electric signal fed back from the object is less than or equal to a predetermined strength.

The substrate is formed of a fixed material that is not deformed by external pressure or a flexible material that is deformed by external pressure.

According to another aspect, there is provided a manufacturing method of the micro probe array device including (1) a process of sequentially patterning aluminum, a silicon oxide layer, and a photoresist on the rear surface of a silicon wafer; (2) a process of an anisotropic etching on the aluminum electrode patterned on the rear surface of the silicon wafer; (3) a process of removing the photoresist and depositing a silicon oxide layer in the region between the silicon cylinders, and oxygen plasma treatment; (4) a process of a wet etching filling an flexible material in a region between the silicon cylinders and removing the flexible material remaining on the silicon cylinders; (5) a process of patterning a silicon oxide layer and a photoresist on the front surface of the silicon wafer; (6) a process of an anisotropic etching for the electrode of a micro probe; (7) a process of removing the photoresist and the oxide layer and manufacturing the micro probe based on wet etching; (8) a process of treating oxygen plasma and depositing a photoresist; (9) a process of selectively etching the photoresist through a first self-alignment process; (10) a process of depositing a conductive material for generating an electrode of the micro probe; (11) a process of removing the photoresist through lift-off, and remaining the conductive material only in the tip region of the micro probe; (12) a process of depositing an insulating material on the front surface of the silicon wafer; (13) a process of spin-coating a photoresist on the front surface of the silicon wafer, and an selectively etching the insulating material on the tip region of the micro probe through a second self-alignment process; and (14) a process of removing and dicing the silicon oxide layer protecting the aluminum electrode on the rear surface of the silicon wafer.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects, features, and advantages of the invention will become apparent and more readily appreciated from the following description of example embodiments, taken in conjunction with the accompanying drawings of which:

FIG. 1 illustrates a result of implanting a micro probe array device into an object.

DETAILED DESCRIPTION

Figure 1:
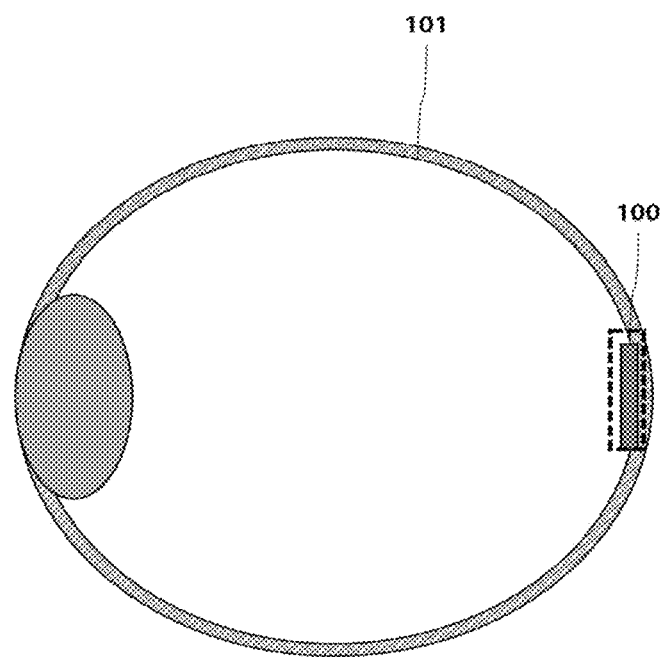
FIG. 1 illustrates a measuring device having a pipette type patch clamp according to an example embodiment.

Hereinafter, some example embodiments will be described in detail with reference to the accompanying drawings. Like reference numerals in the drawings refer to like elements throughout the present disclosure. Various modifications may be made to the example embodiments. Here, the examples are not construed as limited to the disclosure and should be understood to include all changes, equivalents, and replacements within the idea and the technical scope of the disclosure. Although terms of "first," "second," and the like are used to explain various components, the components are not limited to such terms. These terms are used only to distinguish one component from another component.

The terminology used herein is for the purpose of describing particular embodiments only and is not intended to be limiting. As used herein, the singular forms are intended to include the plural forms as well, unless the context clearly indicates otherwise. It will be further understood that the terms "comprises" and/or "comprising," when used in this specification, specify the presence of stated features, integers, steps, operations, elements, components or a combination thereof, but do not preclude the presence or addition of one or more other features, integers, steps, operations, elements, components, and/or groups thereof.

Unless otherwise defined herein, all terms used herein including technical or scientific terms have the same meanings as those generally understood by one of ordinary skill in the art. Terms defined in dictionaries generally used should be construed to have meanings matching contextual meanings in the related art and are not to be construed as an ideal or excessively formal meaning unless otherwise defined herein.

When describing the examples with reference to the accompanying drawings, like reference numerals refer to like constituent elements and a repeated description related thereto will be omitted. In the description of examples, detailed description of well-known related structures or functions will be omitted when it is deemed that such description will cause ambiguous interpretation of the present disclosure.

Hereinafter, example embodiments will be described in detail with reference to the accompanying drawings.

FIG. 1 illustrates a result of implanting a micro probe array device into an object.

Referring to FIG. 1, a micro probe array device 100 may be disposed in a tissue (hereinafter, referred to as an object) 101 that provides an electrical signal or generates an electrical signal. For example, the object may be a tissue such as retina or nerve cell of a human. The micro probe array device 100 may be manufactured according to a semiconductor process. In the micro probe array device 100, a plurality of electrodes may be arranged in an array form. The micro probe array device 100 may provide an electric signal by individually addressing a plurality of electrodes having a size of a micro unit. Here, the tip regions of the plurality of electrodes may be configured in a probe shape.

The micro probe array device 100 according to the first embodiment of the present invention may include a plurality of electrodes having different heights.

The micro probe array device 100 according to the second embodiment of the present invention may include at least one double electrode in which a working electrode and a counter electrode are integrated. The working electrode and the counter electrode provide paths forming an electrical flow through which an electrical signal travels through an object.

The substrate included in the micro probe array device 100 of the third embodiment of the present invention may be formed of a flexible material.

Figure 2:
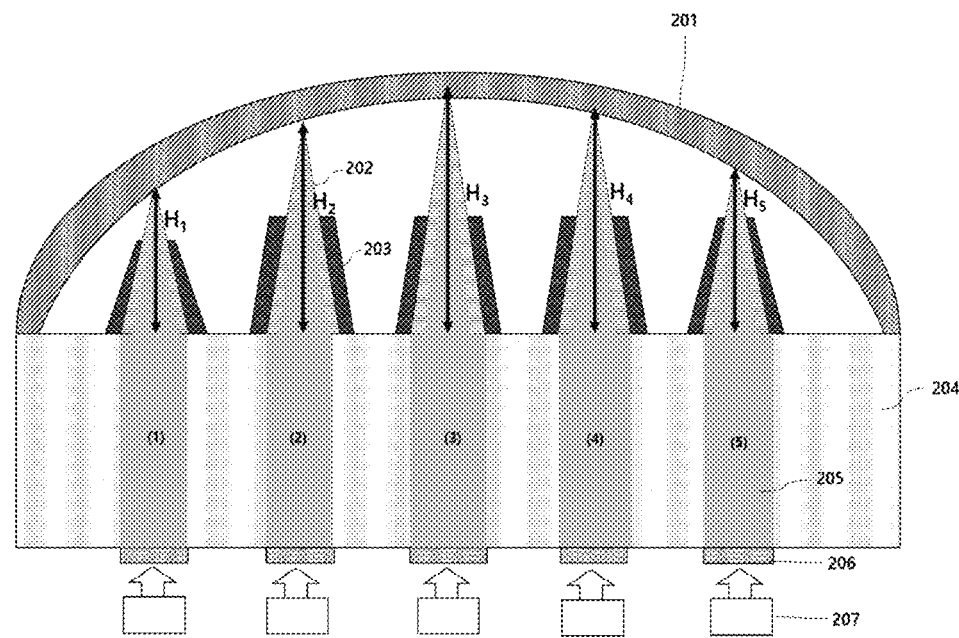
FIG. 2 illustrates a micro probe array device of a first embodiment including electrodes having different heights.

FIG. 2 illustrates a micro probe array device of a first embodiment including electrodes having different heights.

Referring to FIG. 2, the micro probe array device may include a working electrode 202, an insulating layer 203, a substrate 204, a via contact 205, and a reference electrode 206. The micro probe array device includes a plurality of working electrodes 202 and 1-5, and the plurality of working electrodes 1-5 may be spaced apart by a predetermined interval, so that individual addressing may be possible. In the working electrode 202, a tip region has a probe shape. The size of tip area of the working electrode 202 is set to be small in the form of a probe, so that it is easy to insert the object 201 such as a cell. For example, the working electrode 202 may be configured in a conical, triangular pyramid, or square pyramid shape, but may also have a cylindrical shape.

Referring to FIG. 2, an insulating layer 203 is disposed around the working electrode 202. An insulating layer 203 is disposed on the inclined surface of the working electrode 202. Specifically, the insulating layer 203 is disposed on a part of the inclined surface of the working electrode 202, and the insulating layer 203 may not be disposed in the tip region of the working electrode 202. Since the working electrodes 202 adjacent to each other are disposed independently of each other by the insulating layer 203, it is possible to individually address each of the working electrodes 202.

The working electrode 202 is connected to the reference electrode 206 through a via contact 205. The via contacts 205 may be spaced apart from the substrate 204 according to a preset interval and may be disposed independently of each other. Since the via contacts 205 are separated by a substrate 204 made of an insulator, they are disposed to be spaced apart from each other. The tip region of the working electrode 202 may contact the object 201 to provide an electric signal transmitted through the via contact 205 to the object 201 or obtain an electric signal transmitted from the object 201.

The via contact 205 is made of a conductive material to provide a path for an electrical signal that moves between the working electrode 202 and the reference electrode 206. The via contacts 205 may be disposed independently of each other in the substrate 204 according to a preset space. Thus, the working electrodes 202 connected to the via contact 205 can individually address each other without interference.

The electric signal input through the reference electrode 206 is provided to the working electrode 202 through the via contact 205. The tip area of the working electrode 202 may have a probe shape and may contact the object 201. Thus, the electrical signal output from the working electrode 202 is transmitted to the object 201. Alternatively, the electric signal generated by the object 201 may be transmitted to the working electrode 202.

In this case, the plurality of working electrodes 202 in the micro probe array device do not all have the same height. In other words, the micro probe array device may include at least one working electrode 202 having different heights. That is, the micro probe array device may include working electrodes 202 having a height difference.

Referring to FIG. 2, the height of the working electrode 202 may be set corresponding to a shape or the curvature of the object 201. Since the intermediate region of the object 201 is farthest from the substrate 204, the height H3 of the working electrode 3 located in the intermediate region of the object 201 may be the largest. The height of the working electrode 202 may vary depending on the shape or the curvature of the object 201 and the distance between the substrate 204 and the object 201. The height of the working electrode 202 may be set to correspond to a distance between the substrate 204 and the object 201.

Referring to FIG. 2, the micro probe array device may further include an actuator 207. The actuator 207 may apply mechanical pressure to the reference electrode 206. The mechanical pressure means a pressure applied perpendicularly to the reference electrode 206. The tip region of the working electrode 202 is inserted deeper into the object 201 according to the mechanical pressure applied by the actuator 207 to the reference electrode 206. The actuator 207 may be disposed on each of the reference electrodes 206 in the same number as the number of the reference electrodes 206 or may be disposed only one so as to be commonly applied to the reference electrode 206. Alternatively, the actuator 207 may be allocated one for each specific area in the micro probe array device.

The depth at which the tip region of the working electrode 202 is inserted into the object 201 varies according to the strength of the mechanical pressure. That is, as the mechanical pressure increases, the tip region of the working electrode 202 is inserted deeper into the object 201. In this case, the mechanical pressure may be adjusted based on an electrical signal fed back from the object 201.

When the strength of the electric signal fed back from the object 201 is less than a specific reference strength, it may be determined that the contact degree between the tip region of the working electrode 202 and the object 201 is small. Then, as the strength of the electric signal fed back from the object 201 decreases, the mechanical pressure of the actuator 207 increases. As the mechanical pressure increases, the degree of contact between the tip region of the working electrode 202 and the object 201 increases. The mechanical pressure can be set individually differently for the working electrode 202.

In FIG. 2, the insulating layer 203 or the substrate 204 is made of a transparent material so that the position or degree of insertion of the tip region of the working electrode 202 into the object 201 can be confirmed in the rear surface of the micro probe array device. The substrate 204 may be composed of a fixed material such as glass or may be composed of a flexible material such as PDMS. That is, the substrate 204 may or may not be deformed by an external force depending on the material.

Figure 3:
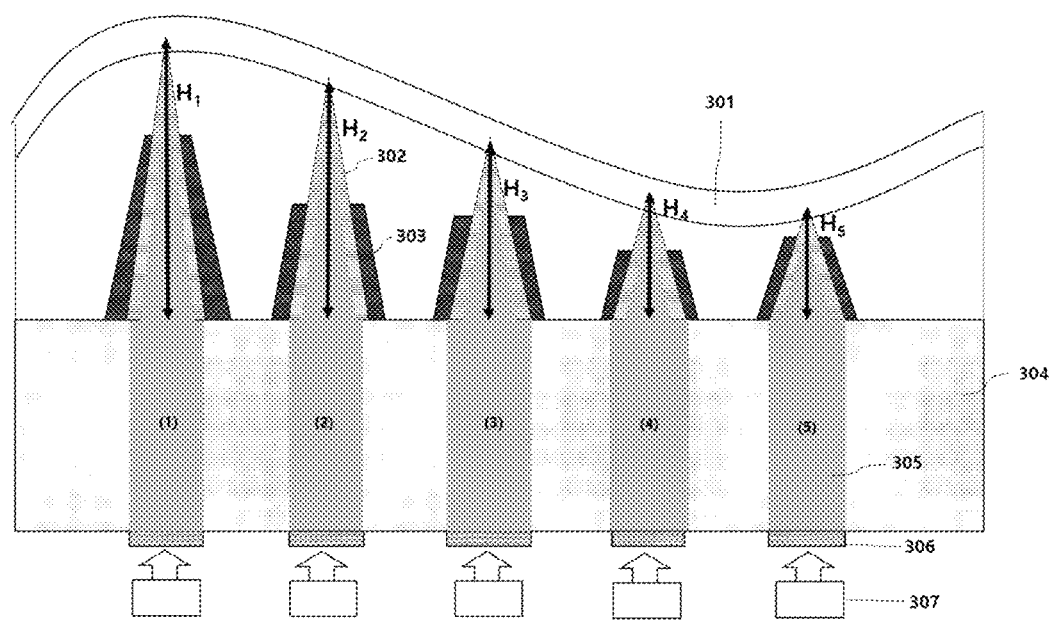
FIG. 3 illustrates a result of adjusting the height according to the curvature of an object in the micro probe array device of the first embodiment.

FIG. 3 illustrates a result of adjusting the height according to the curvature of an object in the micro probe array device of the first embodiment.

Referring to FIG. 3, unlike FIG. 2, it is shown that the height of the working electrode 302 is set differently according to the area of the substrate 304. That is, the height of the working electrode 302 may be set differently in the entire area of the substrate 304. The height of the working electrode 302 is set differently so as to be in close contact with the object 301.

Referring to FIG. 3, the micro probe array device may include a working electrode 302, an insulating layer 303, a substrate 304, a via contact 305, and a reference electrode 306. In addition, the micro probe array device may further include an actuator 307. The working electrode 302, the insulating layer 303, the substrate 304, the via contact 305, and the reference electrode 306 are described in the working electrode 202, the insulating layer 203, and the substrate 204, the via contact 205, and the reference electrode 206.

FIG. 3 shows that the distance between the object 301 and the substrate 304 is the largest in the left area of the object 301 than in the middle area of the object 301, unlike FIG. 2. Therefore, the height of the working electrode 1 is larger than that of the other working electrodes 2-5. According to an embodiment of the present invention, the height of the working electrode 302 may be adaptively changed (increased or decreased) through external manipulation or the like. Alternatively, although the height of the working electrode 302 is fixed, the tip region of the working electrode 302 moves in the direction of the object 301 according to the mechanical pressure applied by the actuator 307 to the reference electrode 306, and the degree of the contacts that the tip area of the working electrode 302 contacts the object 301 may increase.

Figure 4:
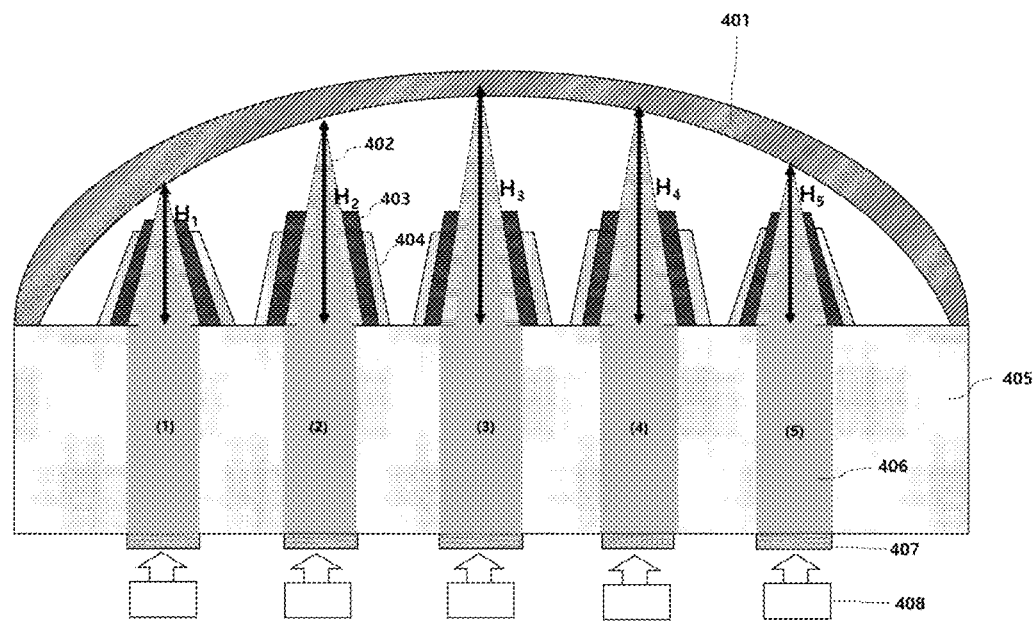
FIG. 4 illustrates a result of applying a double electrode in the micro probe array device of the first embodiment.

FIG. 4 illustrates a result of applying a double electrode in the micro probe array device of the first embodiment.

The micro probe array device shown in FIG. 4 includes a working electrode 402, an insulating layer 403, a counter electrode 404, a substrate 405, a via contact 406, and a reference electrode 407. The description about the working electrode 402, the insulating layer 403, the substrate 405, the via contact 406, and the reference electrode 407 is same as the description about the working electrode 202, the insulating layer 203, and the substrate 204, the via contact 205, and the reference electrode 206 shown in FIG. 2.

In FIG. 4, there are an insulating layer 403 between the working electrode 402 and the counter electrode 404, unlike FIG. 2. In other words, the insulating layer 403 can separate the working electrode 402 and the counter electrode 404 from each other. Electrical flows may be formed between the working electrode 402, the object 401, and the counter electrode 404. For example, the electrical signal output from the working electrode 402 is transmitted to the object 401 in contact with the working electrode 402, and the electrical signal output from the object 401 may be transmitted to the counter electrode 404. have. Although not shown in FIG. 4, an insulating layer may be further located outside the counter electrode 404.

FIG. 5 to 12 illustrate a method of manufacturing a micro probe array device according to the first embodiment.

Figure 5:
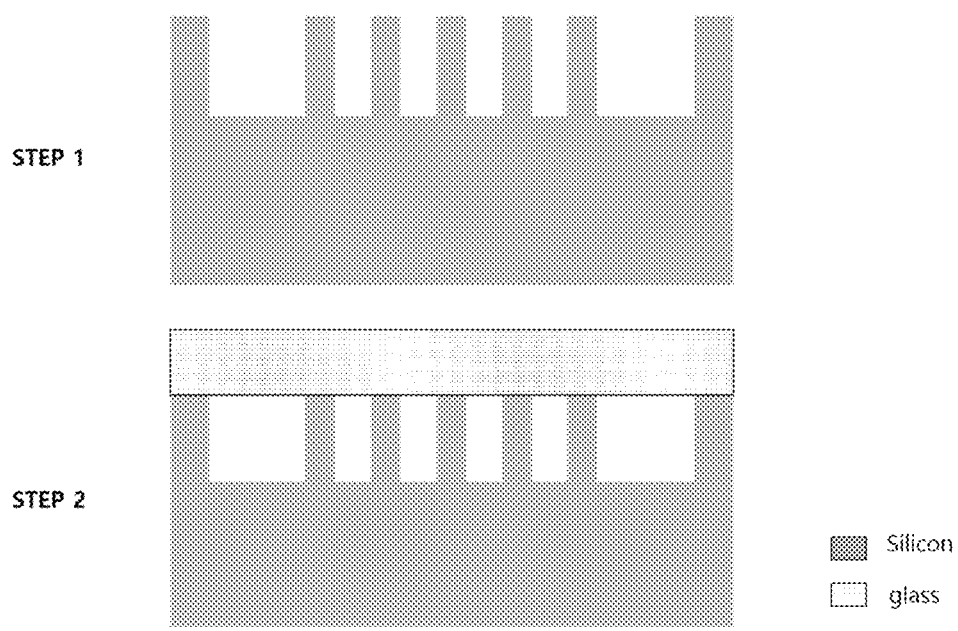
FIG. 5 to 12 illustrate a method of manufacturing a micro probe array device according to the first embodiment.

In STEP 1 of FIG. 5, a process of forming a plurality of cylinders in an array form is performed. Here, the cylinder may be made of silicon. A plurality of cylinders as shown in STEP 1 of FIG. 5 may be formed in an array form by vertically etching the remaining area on the rear surface of the silicon wafer according to the Deep Reactive Ion Etching (DRIE) process except for an area corresponding to a plurality of cylinders. Each of the plurality of cylinders represents an individual addressing structure.

In STEP 2 of FIG. 5, a process of anodic bonding the silicon wafer and the glass wafer is performed. The silicon wafer and the glass wafer may be combined in a vacuum state (1E−3 torr) so that glass may be filled in the region where the silicon wafer is etched. The substrate is composed of the glass.

Figure 6:
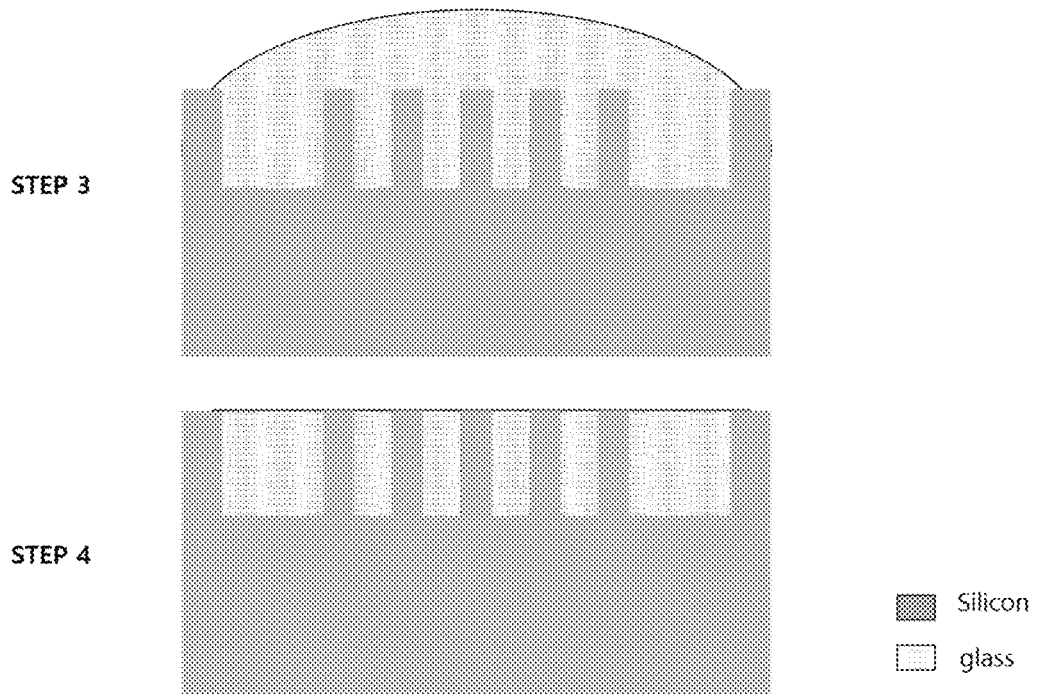

In STEP 3 of FIG. 6, a reflow process of filling the glass in the silicon-etched region is performed.

In STEP 4 of FIG. 6, a process of removing the glass wafer existing on the upper portion of the silicon wafer through chemical/mechanical polishing (CMP) is performed.

Figure 7:
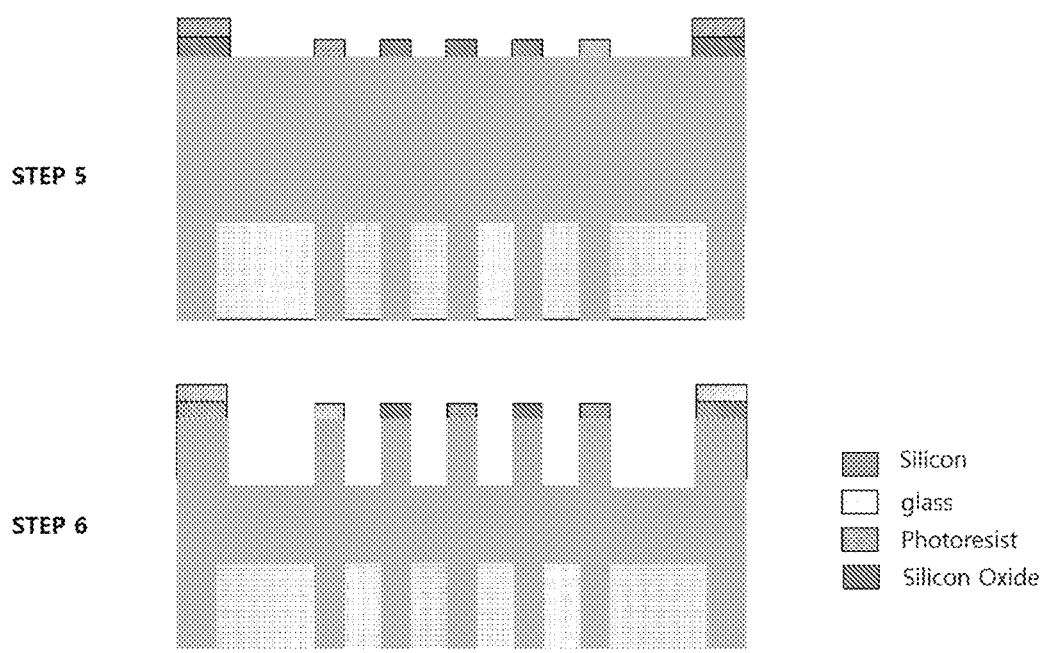

In STEP 5 of FIG. 7, a process of patterning the silicon oxide and a photoresist is performed on the front surface of the silicon wafer, which is the opposite surface of the rear surface of the silicon wafer filled with the glass wafer. Silicon oxide and photoresist are patterned at the location of the silicon pillar. The number of silicon pillars having different heights may be determined according to the material to be patterned. In STEP 5, the height of the silicon pillar at the position where only the photoresist is patterned is lower than the height of the silicon pillar at the position where only the silicon oxide is patterned. In addition, the height of the silicon pillar may be adjusted through the number of patterned materials.

In STEP 6 of FIG. 7, a process of a first anisotropic etching is performed on the front surface of the silicon wafer in which the silicon oxide and the photoresist are patterned on the silicon wafer. The anisotropic etching process is performed as a DRIE process. An array of silicon cylinders is formed according to the anisotropic etching process. In STEP 6, the etch depth formed by the first anisotropic etching corresponds to the height of the small silicon pillars among the silicon pillars arranged in an array form.

Figure 8:
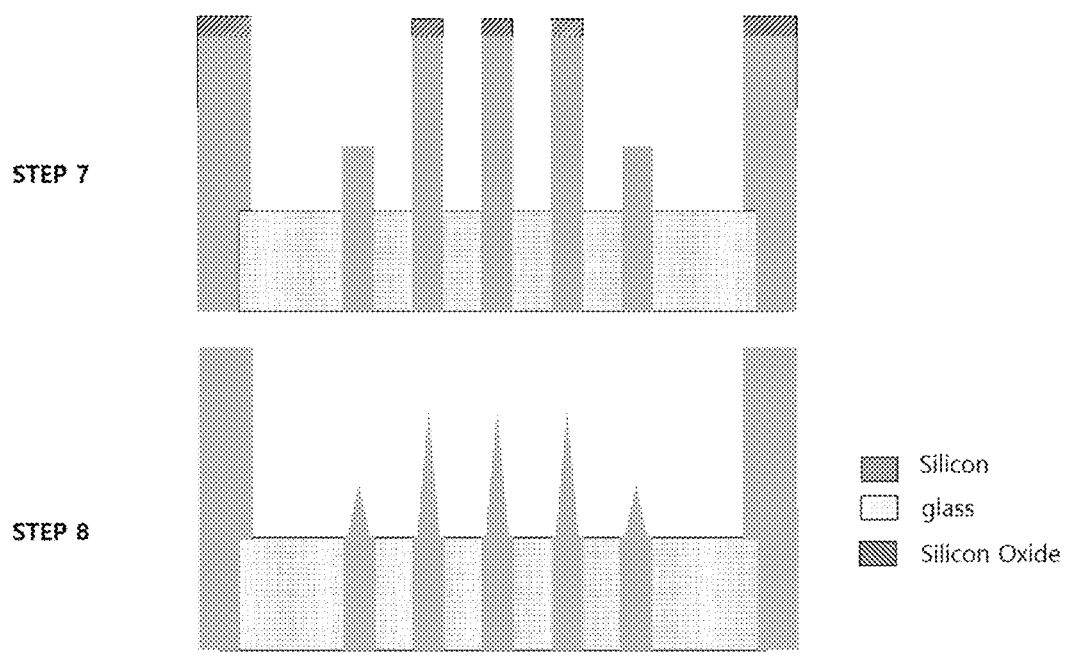

In STEP 7 of FIG. 8, a process of removing the photoresist and a second anisotropic etching is performed. The etch depth in STEP 7 formed by the second anisotropic etching corresponds to the height of the tallest silicon pillars among silicon cylinders arranged in an array form. The anisotropic etching process is performed as a DRIE process. In addition, a difference of the height between silicon cylinders may be determined according to the second etching depth. That is, according to STEP 7, silicon cylinders having different heights may be disposed in the array of silicon cylinders through two anisotropic etching processes.

In STEP 8 of FIG. 8, a process of removing the silicon oxide layer with a hydrofluoric acid solution, and a silicon isotropic wet etching is performed. Isotropic wet etching is performed using a solution in which hydrofluoric acid and nitric acid are mixed, and accordingly, a micro probe area having a tip region in a probe shape may be formed. Via contacts that can be individually addressed are formed through STEP 8.

Figure 9:
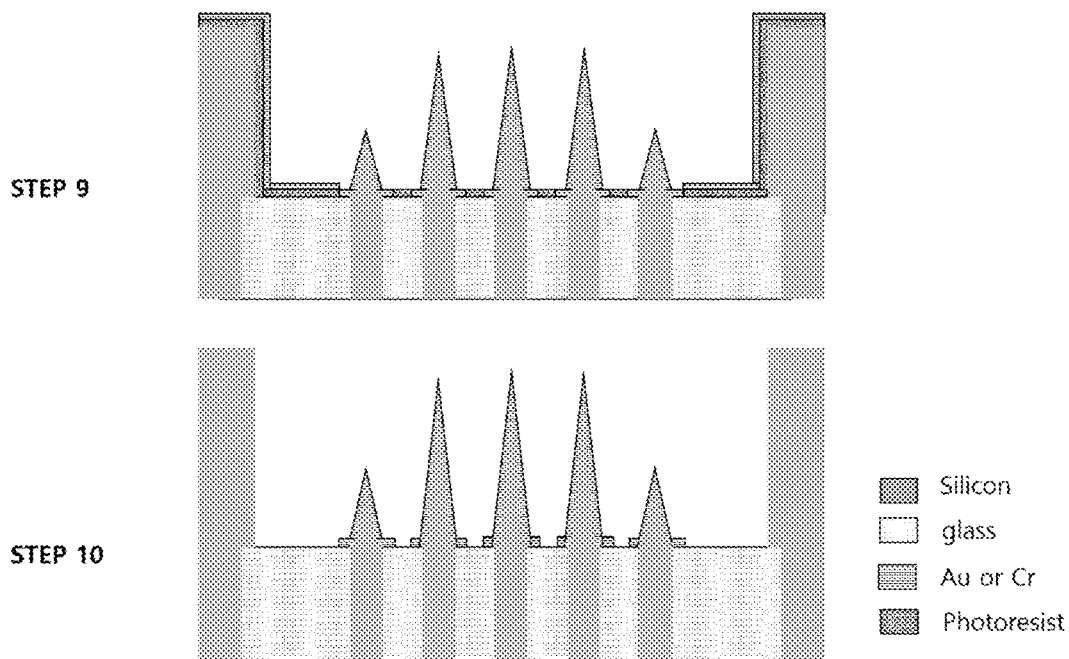

In STEP 9 of FIG. 9, a photoresist is patterned on the micro probe area according to photolithography, and then a process of depositing a conductive material (chrome or gold) is performed. The conductive material constitutes the working electrode.

In STEP 10 of FIG. 9, a process of lifting-off is performed to remove the photoresist from the micro probe area and only the conductive material deposited on the micro probe remains.

Figure 10:
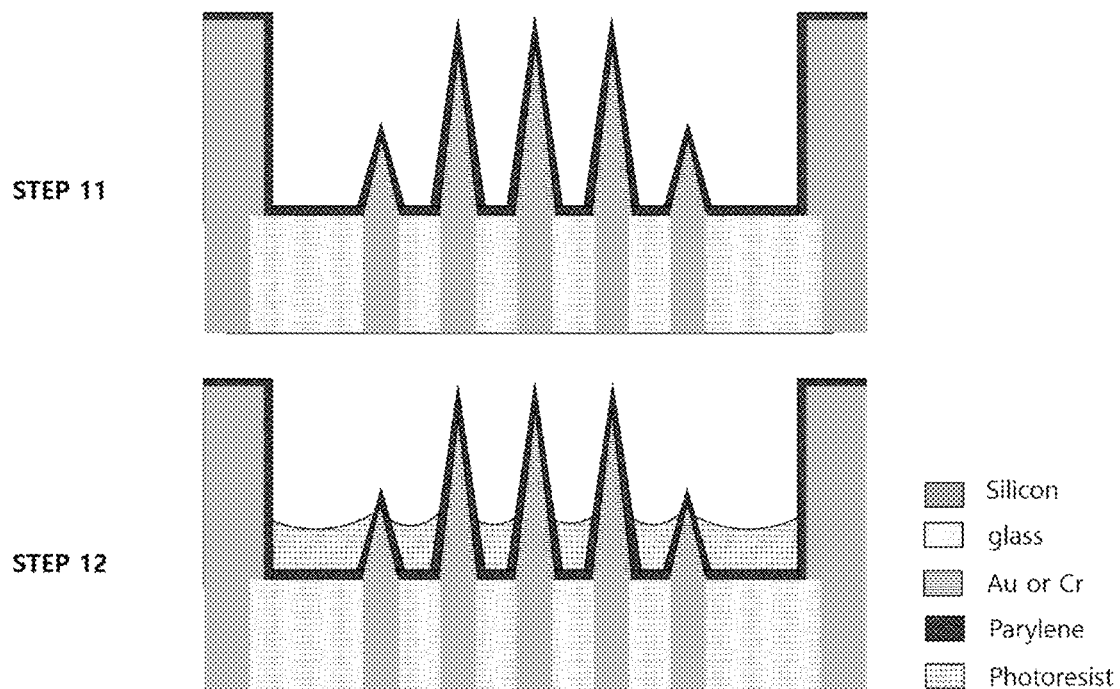

In STEP 11 of FIG. 10, a process of depositing an insulating material on the micro probe region is performed. For example, the insulating material may be parylene. The region on which the insulating material is deposited corresponds to the insulating layer.

In STEP 12 of FIG. 10, a process of spin coating a photoresist on the micro probe region is performed. Spin coating is performed so that the photoresist in the tip region of the micro probe is coated thinner than other portions. That is, the photoresist is coated to a position where the conductive material is not covered by the insulating material and the electrode made of the conductive material can be exposed to the outside.

Figure 11:
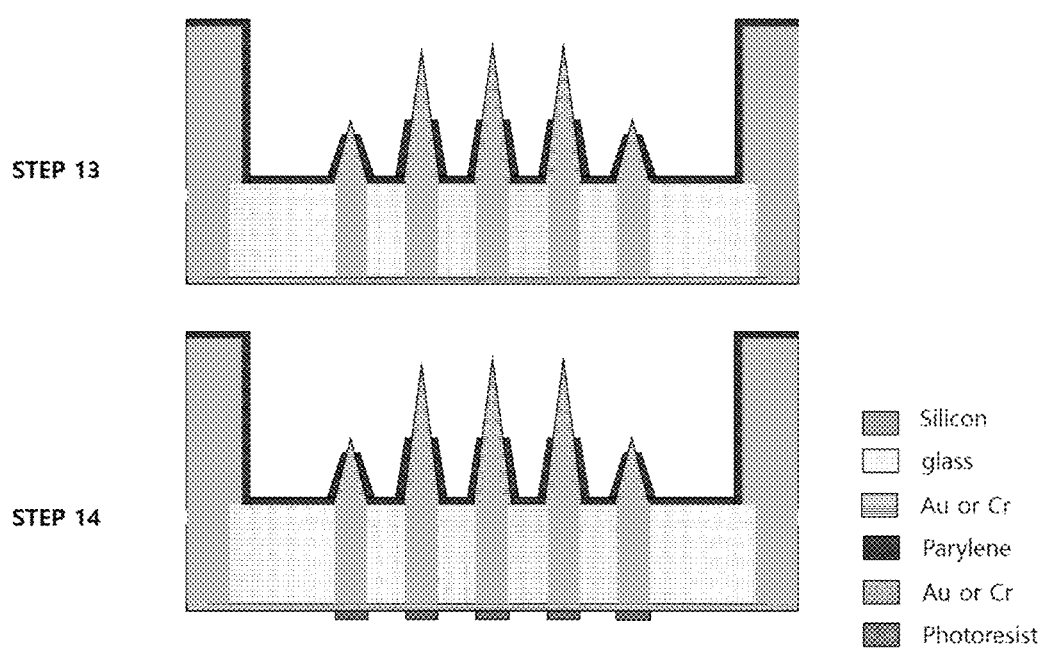

In STEP 13 of FIG. 11, a process of etching a photoresist through a self-alignment process and depositing a conductive material on the rear surface of the glass wafer is performed. According to STEP 13, the working electrode and the insulating layer of the micro probe array device are formed. According to STEP 13, a specific area of the working electrode may be covered by the insulating layer, and the tip area of the working electrode may be exposed without being covered by the insulating layer. The specific area is remaining area except for the tip area in entire area of the working electrode. In addition, the conductive material deposited on the rear surface of the glass wafer includes chromium or gold and may be an electrode material of the reference electrode.

In STEP 14 of FIG. 11, a process of patterning a photoresist on the conductive material deposited on the rear surface of the glass wafer is performed. The photoresist is patterned to correspond to the position of the micro probe.

Figure 12:
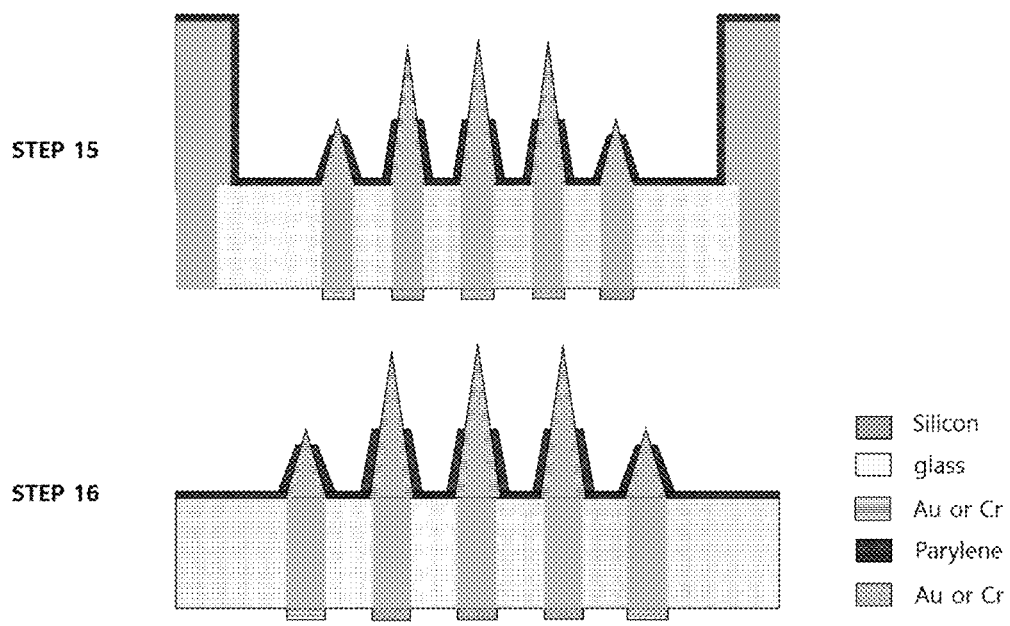

In STEP 15 of FIG. 12, a process of etching the conductive material is performed. The conductive material is etched to form a reference electrode that provides an electrical signal for individual addressing to the working electrode in the form of a micro probe.

In STEP 16 of FIG. 12, a process of dicing is performed to remove silicon at the edge so that the micro probe array device can be implanted on the object.

According to an embodiment of the present invention, patterning is performed through a photolithography process of different materials. In addition, by using the material patterned in the Deep Reactive Ion Etching (DRIE) process as a mask for silicon etching, an array structure composed of a plurality of silicon pillars having different heights is formed.

In the micro probe array device, as the area of the electrode region increases, the height of the working electrode having the smallest height among the working electrodes decreases. However, in the micro probe array device, as the area of the electrode region increases, the difference (step difference) between the height of the working electrode having the largest height among the working electrodes and the height of the working electrode having the smallest height increases.

According to an exemplary embodiment of the present invention, a uniform electric signal may be provided to the object by setting the height of the working electrode to enable the same contact according to the curvature of the object.

In addition, a micro probe array device (e.g., an artificial retinal prosthesis device) configured with a plurality of micro probe-shaped working electrodes may be manufactured using a semiconductor process. In particular, according to an embodiment of the present invention, it is possible to fabricate a uniform and reproducible micro probe array device according to a wafer unit process FIG. 13 illustrates a micro probe array device of a second embodiment including a double electrode.

Figure 13:
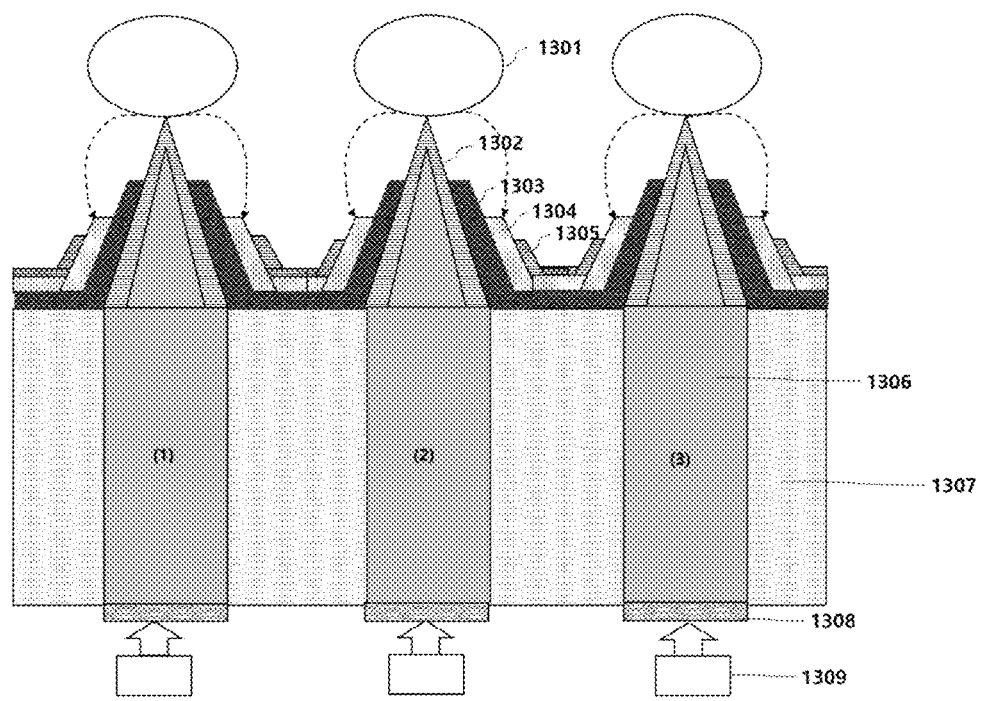
FIG. 13 illustrates a micro probe array device of a second embodiment including a double electrode.

Referring to FIG. 13, the micro probe array device includes a working electrode 1302, a first insulating layer 1303, a counter electrode 1304, a second insulating layer 1305, and a via contact. 1306), a substrate 1307, and a reference electrode 1308. The micro probe array device includes a plurality of working electrodes 1302 and 1-5, and the plurality of working electrodes 1-5 may be spaced apart by a predetermined interval, so that individual addressing may be possible. In the working electrode 1302, a tip region has a probe shape. The size of the tip area of the working electrode 1302 is set to be small in the shape of a probe, so that it is easy to insert the object 1301 such as a cell. For example, the working electrode 1302 may be configured in a conical, triangular pyramid, or square pyramid shape, but may also have a cylindrical shape.

The substrate 1307 may be made of a fixed material such as glass or a flexible material such as PDMS. When the substrate 1307 is made of a flexible material, the shape of the substrate 1307 may be changed according to an external force. When the shape of the substrate 1307 is changed according to an external force, the position of the tip area of the working electrode 1302 is also changed, so that the contact degree between the working electrode 1302 and the object 1301 may also vary.

Referring to FIG. 13, the working electrode 1302 and the counter electrode 1304 are separated by a first insulating layer 1303. The first insulating layer 1303 is disposed on the inclined surface of the working electrode 1302. In addition, a second insulating layer 1305 is disposed on the inclined surface of the counter electrode 1304. A flow of an electric signal may be formed between the working electrode 1302, the counter electrode 1304, and the object 1301 connected to the working electrode 1302. For example, the electrical signal output from the working electrode 1302 is transmitted to the object 1301 in contact with the working electrode 1302, and the electrical signal output from the object 1301 may be transmitted to the counter electrode 1304. have. The working electrode 1302 and the counter electrode 1304 are integrated to form a double electrode.

In the case of FIG. 13, one double electrode composed of one counter electrode 1304 on one working electrode 1302 is shown, but the present invention includes a plurality of counter electrodes 1304 on one working electrode 1302. It does not exclude a plurality of configured double electrodes. When a plurality of counter electrodes 1304 are present, an insulating layer 1305 may be disposed between the counter electrodes 1304.

According to the embodiment of the present invention, since the working electrode 1302 and the counter electrode 1304 are integrated to form a double electrode, the working electrode 1302 having a more micro probe shape can be disposed in the same area. have. In addition, since the working electrodes 1302 are spaced apart by a predetermined interval and are divided into a first insulating layer 1303 and a second insulating layer 1305, there is little interference between the working electrodes 1302. In addition, since the working electrode 1302 is in the form of a probe, a local stimulation is possible, so that the effect of the electric signal on the adjacent region of the object 1301 is small.

Referring to FIG. 13, a first insulating layer 1303 is disposed around the working electrode 1302. The first insulating layer 1303 is disposed on the inclined surface of the working electrode 1302. Specifically, the insulating layer 1303 may be formed on a part of the inclined surface of the working electrode 1302, and the insulating layer 1303 may not be formed in the tip region of the working electrode

1302. Since the working electrodes 1302 adjacent to each other are disposed independently of each other by the insulating layer 1303, individual addressing is possible for each of the working electrodes 1302.

Similarly, the counter electrode 1304 is disposed on the inclined surface of the first insulating layer 1303. Then, the second insulating layer 1305 is disposed on the inclined surface of the counter electrode 1304. The first insulating layer 1303 may be disposed on a part of the inclined surface of the working electrode 1302. In other words, a specific area of the inclined surface of the working electrode 1302 may be exposed without being covered by the first insulating layer 1303, and the remaining area of the inclined surface is covered by the first insulating layer 1303. The specific area corresponds to the tip area of the working electrode 1302.

Further, the counter electrode 1304 may be disposed on a part of the inclined surface of the first insulating layer 1303. A specific area of the inclined surface of the first insulating layer 1303 may be exposed without being covered by the counter electrode 1304, and the remaining area of the inclined surface of the first insulating layer 1303 is covered by the counter electrode 1304.

The second insulating layer 1305 may be disposed on a part of the inclined surface of the counter electrode 1304. In other words, a specific part of the inclined surface of the counter electrode 1304 may be exposed without being covered by the second insulating layer 1305, and the rest part of the inclined surface is covered by the second insulating layer 1305.

Thus, referring to FIG. 13, a working electrode 1302, a first insulating layer 1303, a counter electrode 1304, and a second insulating layer 1305 are sequentially disposed. In addition, as shown in FIG. 2, the working electrode 1302, the first insulating layer 1303, the counter electrode 1304, and the second insulating layer 1305 are sequentially decreased in length. The working electrode 1302 is electrically separated from the counter electrode 1304 by a first insulating layer 1303. In addition, a specific part of the working electrode 1302 may be covered by the first insulating layer 1303, and the remaining part of the working electrode 1302 may be exposed to the outside without being covered by the first insulating layer 1303. The remaining part of the working electrode 1302 corresponds to the tip area of the working electrode 1302. In particular, since the tip region of the working electrode 1302 must contact the object 1301, it is not covered by the first insulating layer 1303.

The working electrode 1302 is connected to the reference electrode 1308 through a via contact 1306. A working electrode 1302 is disposed on the top of the via contact 1306, and a reference electrode 1308 is disposed on the bottom of the via contact 1306. The via contacts 1306 may be disposed independently of each other in the substrate 1307 according to a preset interval. Since the via contacts 1306 are separated by the substrate 1307 made of an insulator, they are disposed to be spaced apart from each other. The tip region of the working electrode 1302 may contact the object 1301 to provide an electrical signal transmitted through the via contact 1306 to the object 1301 or obtain an electrical signal from the object 1301.

The via contact 1306 is made of a conductive material to provide a path for an electrical signal moving between the working electrode 1302 and the reference electrode 1308. The via contacts 1306 may be spaced apart from the substrate 1307 according to a preset interval and may be disposed independently of each other. Thus, the working electrodes 1302 connected to the via contact 1306 can individually address each other without interference.

The electrical signal input through the reference electrode 1308 is provided to the working electrode 1302 through the via contact 1306. The tip region of the working electrode 1302 may have a probe shape and may contact the object 1301. Thus, the electrical signal output from the working electrode 1302 is transmitted to the object 1301. Alternatively, the electric signal generated by the object 1301 may be transmitted to the working electrode 1302.

Referring to FIG. 13, the micro probe array device may further include an actuator 1309. The actuator 1309 may apply mechanical pressure to the reference electrode 1308. Mechanical pressure refers to a pressure applied perpendicularly to the reference electrode 1308. The tip region of the working electrode 1302 is inserted deeper into the object 1301 according to the mechanical pressure applied by the actuator 1309 to the reference electrode 1308. One actuator 1309 may be disposed on each of the reference electrodes 1308 in the same number as the number of the reference electrodes 1308 or may be disposed so as to be commonly applied to the reference electrode 1308. Alternatively, one actuator 1309 may be allocated for each specific area in the micro probe array device.

The depth at which the tip region of the working electrode 1302 is inserted into the object 1301 varies according to the strength of the mechanical pressure. That is, as the mechanical pressure increases, the tip region of the working electrode 1302 is inserted deeper into the object 1301. In this case, the mechanical pressure may be adjusted based on the electrical signal fed back from the object 1301.

When the strength of the electric signal fed back from the object 1301 is less than a specific reference strength, it may be determined that the contact degree between the tip region of the working electrode 1302 and the object 1301 is small. Then, as the strength of the electric signal fed back from the object 1301 decreases, the mechanical pressure of the actuator 1309 increases. As the mechanical pressure increases, the degree of contact between the tip region of the working electrode 1302 and the object 1301 increases. The mechanical pressure may be individually set differently for the working electrode 1302.

In FIG. 13, the first insulating layer 1303, the second insulating layer 1305, or the substrate 1307 is a position or insertion of the tip region of the working electrode 1302 into the object 1301 from the rear surface of the micro probe array device. It may be made of a transparent material so that the degree to which it becomes can be confirmed.

Figure 14:
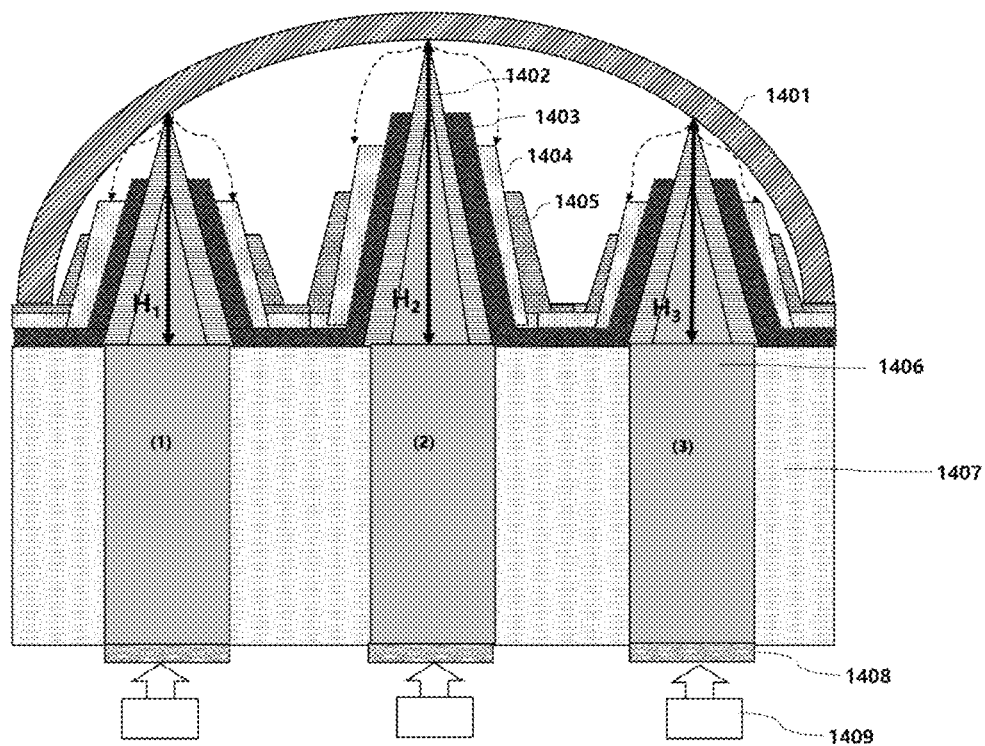
FIG. 14 illustrates the result of adjusting the height of the electrode in the micro probe array device of the second embodiment.

FIG. 14 illustrates the result of adjusting the height of the electrode in the micro probe array device of the second embodiment.

In the micro probe array device illustrated in FIG. 13, the working electrodes 1402 have the same height. However, in the micro probe array device illustrated in FIG. 14, the working electrodes 1402 have different heights so that the working electrodes 1402 can be in close contact with the object 1401 according to the curvature of the object 1401. Referring to FIG. 14, unlike FIG. 13, the height of the working electrode 1402 may be set differently for each area of the object 1401. The distance from the substrate 1407 to the object 1401 is determined differently for each area of the object 1401.

In the case of FIG. 14, unlike FIG. 13, the distance from the substrate 1407 to the object 1401 is different for each area of the micro probe array device due to the curvature of the object 1401. In this case, the height of the working electrode 1402 may be set differently for each region of the micro probe array device.

Referring to FIG. 14, the micro probe array device may include a working electrode 1402, an insulating layer 1403, a substrate 1404, a via contact 1405, and a reference electrode 1406. In addition, the micro probe array device may further include an actuator 1409. The description about the working electrode 1402, the insulating layer 1403, the substrate 1404, the via contact 1405, and the reference electrode 1406 is same as the description about the working electrode 1302, the insulating layer 1303, and the substrate 1304, the via contact 1305, and the reference electrode 1306.

Referring to FIG. 14, it is shown that the distance between the object 1401 and the substrate 1407 is the largest in the middle area of the object 1401 than the rest area. As shown in FIG. 14, since the intermediate region of the object 1401 is farthest from the substrate 1407, the working electrode 2 1402 located in the intermediate region of the object 1401 is the largest with a height H2.

However, the above description is only an example, and the distance between the object 1401 and the substrate 1407 is determined differently according to the shape or curvature of the object 1401, based on the distance between the object 1401 and the substrate 1407 Thus, the height of the working electrode 1402 may be set differently.

According to an embodiment of the present invention, the height of the working electrode 1402 may be adaptively changed (increased or decreased) through external manipulation or the like. Alternatively, although the height of the working electrode 1402 is fixed, the tip region of the working electrode 1402 moves in the direction of the object 1401 according to the mechanical pressure applied by the actuator 1409 to the reference electrode 1408, thereby the degree of contact to which the tip area of the working electrode 1402 contacts the object 1401 may increase.

FIG. 15 to 23 illustrates a method of manufacturing a micro probe array device according to a second embodiment.

Figure 15:
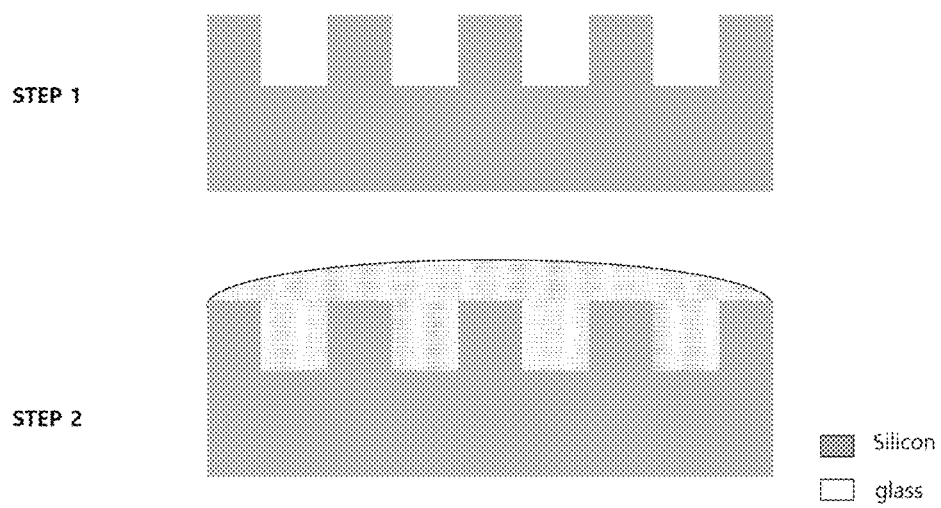
FIG. 15 to 23 illustrates a method of manufacturing a micro probe array device according to a second embodiment.

In STEP 1 of FIG. 15, a process of an anisotropic etching is performed on the rear surface of the silicon wafer for individual addressing of the micro probe. Here, the anisotropic etching is processed according to-Deep Reactive Ion Etching (DRIE). By the process of STEP 1, a plurality of cylinders may be formed in an array. Here, the cylinder may be made of silicon. A plurality of cylinders may be formed in an array form by vertically etching the remaining regions of the silicon wafer while leaving only the cylindrical regions according to the DRIE process. Each of the plurality of cylinders represents an individual addressing structure.

In STEP 2 of FIG. 15, a process of anodic bonding the silicon wafer and the glass wafer to insulate the micro probe and reflowing the glass wafer is performed. The silicon wafer and the glass wafer may be combined in a vacuum state (1E−3 torr) so that glass may be filled in the region where the silicon wafer is etched. The substrate may consist of the glass.

Figure 16:
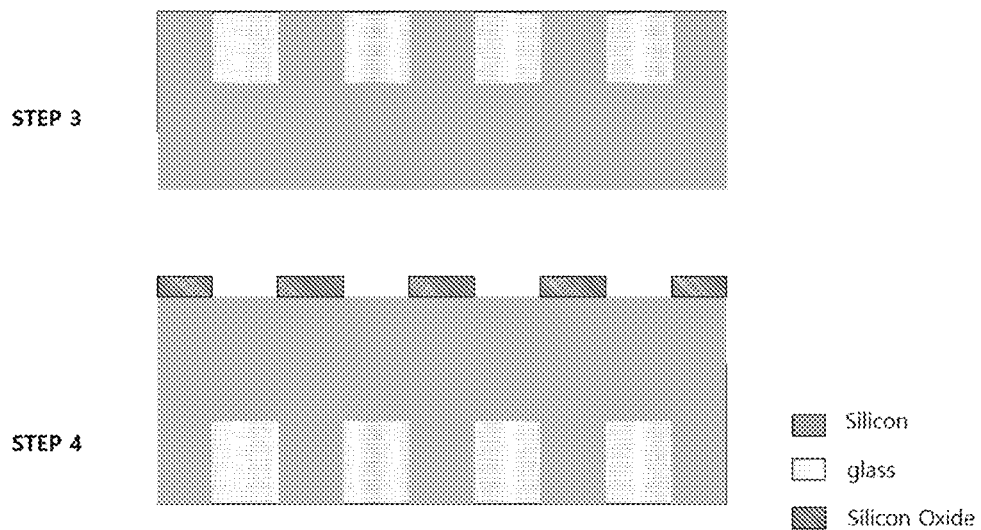

In STEP 3 of FIG. 16, a process of removing glass existing on the silicon wafer by chemical/mechanical polishing (CMP) and reducing the thickness of the silicon wafer by a predetermined size is performed.

In STEP 4 of FIG. 16, a process of depositing the silicon oxide layer, and a patterning to create a silicon cylinder to be a micro probe is performed.

Figure 17:
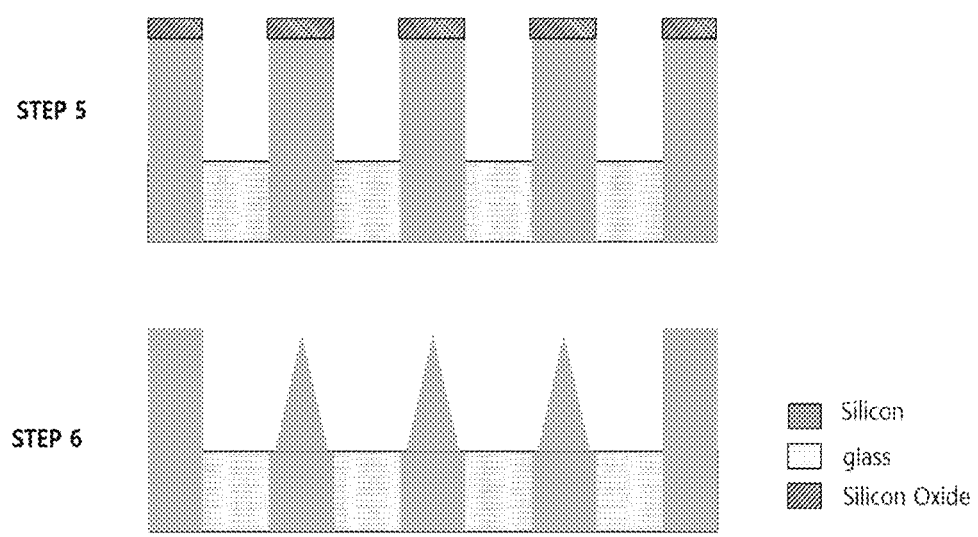

In STEP 5 of FIG. 17, a process of an anisotropic etching process to generate a silicon cylinder to be a micro probe is performed.

In STEP 6 of FIG. 17, a process of removing the photoresist and forming a micro probe having a sharp tip region through wet etching is performed. Isotropic wet etching is performed using a solution in which hydrofluoric acid and nitric acid are mixed, and accordingly, a micro probe area having a tip region in a probe shape may be formed. Via contacts that can be individually addressed are formed through STEP 6.

Figure 18:
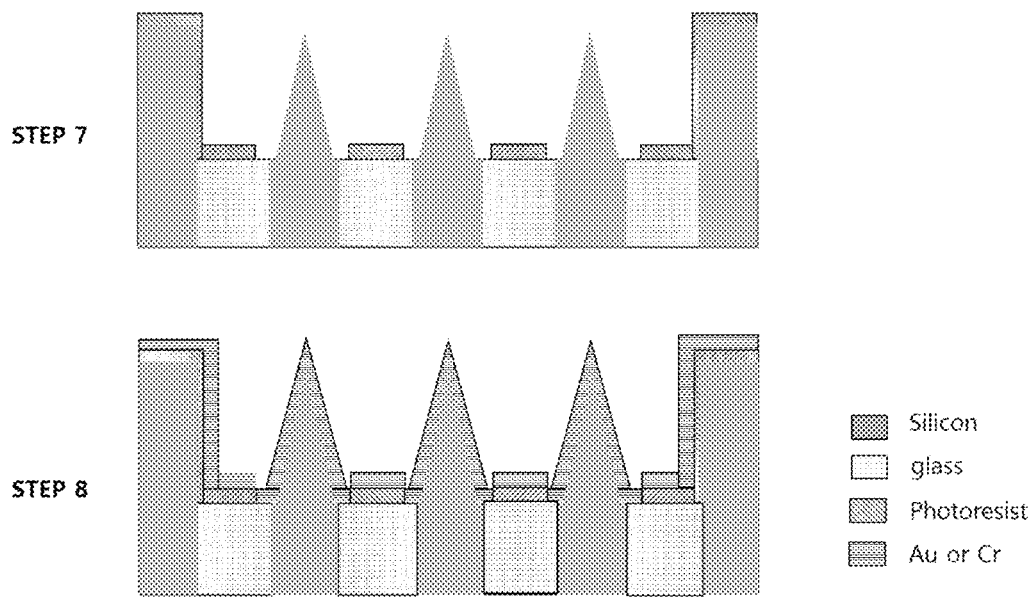

In STEP 7 of FIG. 18, a process of depositing a photoresist and patterning according to photolithography so that a working electrode remains on the micro probe.

In STEP 8 of FIG. 18, a process of depositing a conductive material for forming a working electrode is performed. Here, the conductive material may be gold or chromium, but the present invention is not limited thereto.

Figure 19:
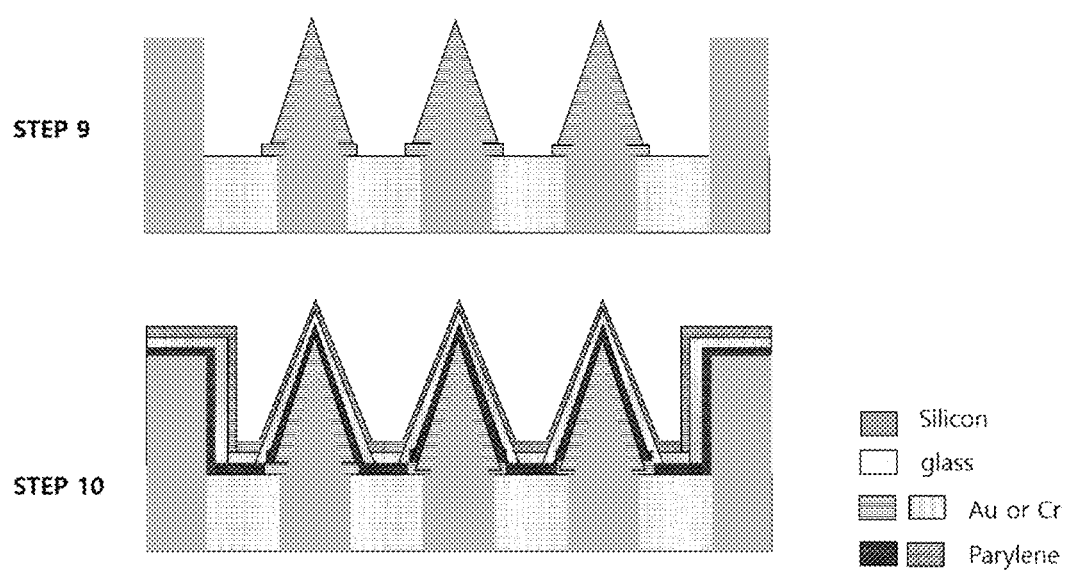

In STEP 9 of FIG. 19, a process of removing the photoresist in the micro probe region and a lift-off in which only the conductive material deposited on the micro probe remains is performed.

In STEP 10 of FIG. 19, a process of depositing parylene as an insulating material and a conductive material (gold or chromium) for forming a counter electrode and then depositing an insulating material (parylene) is performed. Here, parylene as an insulating material becomes a component of the first insulating layer and the second insulating layer in the micro probe array device. The conductive material deposited in STEP 10 is used to form the counter electrode.

Figure 20:
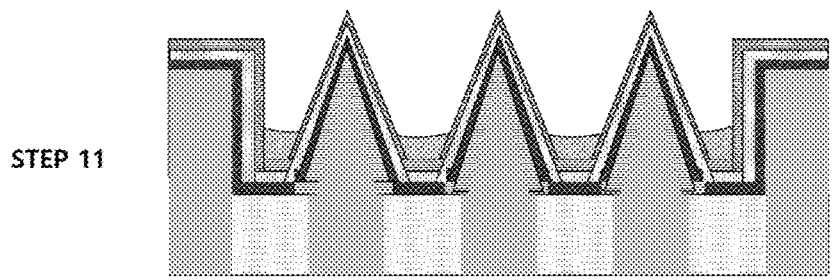
Figure 20:
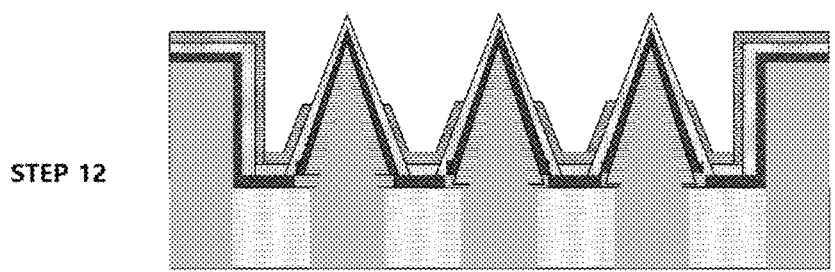

In STEP 11 of FIG. 20, a process of spin coating a photoresist is performed. Here, the photoresist is coated to a position where the second deposited insulating material is etched to expose the second deposited conductive material.

In STEP 12 of FIG. 20, a process of etching the second deposited parylene through a self-alignment process and removing the spin-coated photoresist is performed. According to STEP 12, a second insulating layer of the micro probe array device is formed.

Figure 21:
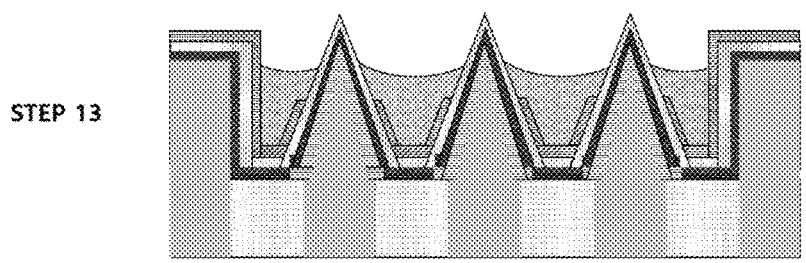
Figure 21:
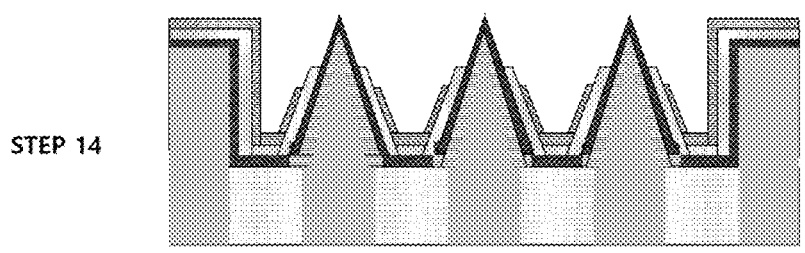

In STEP 13 of FIG. 21, a process of spin coating a photoresist is performed. Here, the photoresist is coated to a position where the second deposited conductive material is etched to expose the first deposited insulating material.

In STEP 14 of FIG. 21, a process of etching the second deposited conductive material through a self-alignment process and removing the spin-coated photoresist is performed. According to STEP 14, the counter electrode of the micro probe array device is formed. Here, the secondly deposited conductive material corresponds to the second insulating layer, and the firstly deposited insulating material corresponds to the counter electrode. According to STEP 14, a portion of the counter electrode may be covered by the second insulating layer, and the rest of the counter electrode may be exposed without being covered by the second insulating layer.

Figure 22:
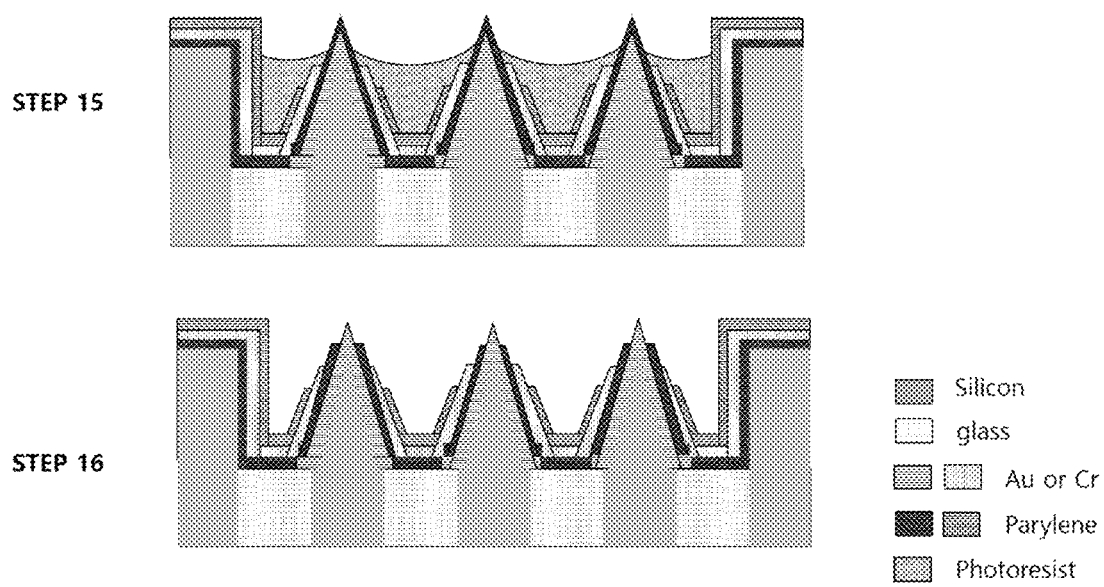

In STEP 15 of FIG. 22, a process of spin coating a photoresist is performed. Here, the photoresist is coated to a position where the first deposited insulating material is etched to expose the first deposited conductive material.

In STEP 16 of FIG. 22, a process of etching the first deposited parylene through a self-alignment process and removing the spin-coated photoresist is performed. According to STEP 16, the working electrode and the first insulating layer of the micro probe array device are formed. According to STEP 16, a portion of the working electrode may be covered by the first insulating layer, and the tip region of the working electrode may be exposed without being covered by the first insulating layer.

Figure 23:
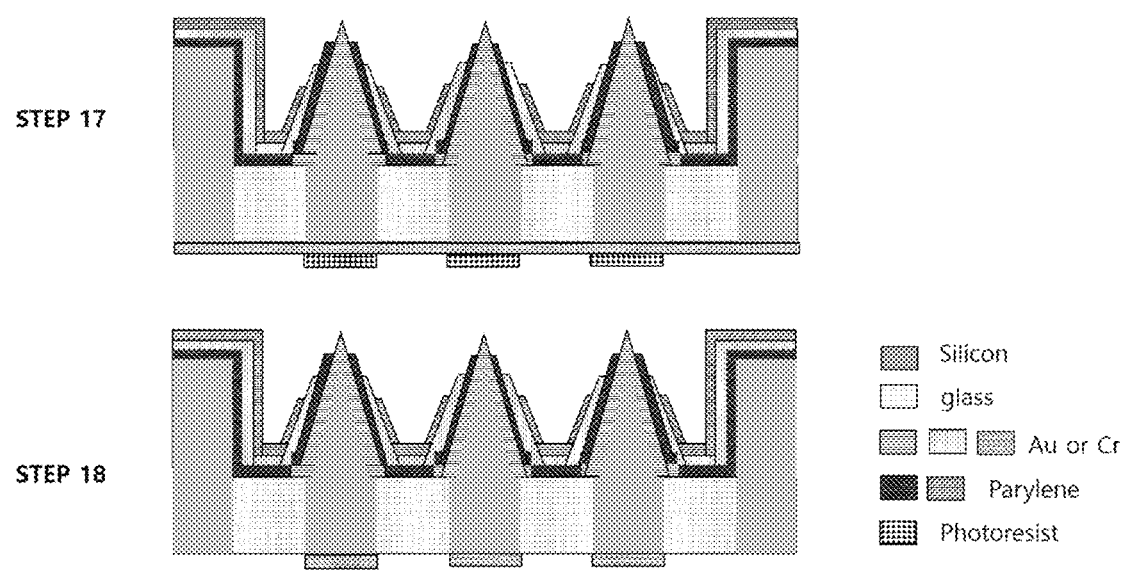

In STEP 17 of FIG. 23, a process of depositing a conductive material on the rear surface of the silicon wafer and depositing a photoresist is performed. This process is to fabricate an addressing line that will deliver current to the micro probe. Here, the conductive material may include gold or chromium. And the conductive material deposited in STEP 17 is used to form the reference electrode.

In STEP 18 of FIG. 23, a process of etching the chromium or gold deposited on the rear surface of the silicon wafer and removing the photoresist is performed. Through this process, the microprobe array device shown in FIG. 13 is manufactured.

Figure 24:
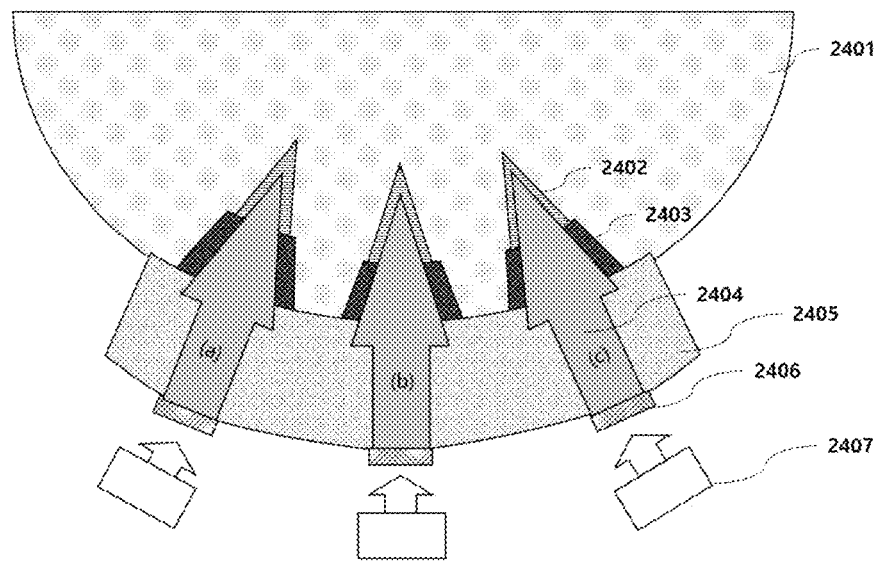
FIG. 24 illustrates a micro probe array device according to a third embodiment.

FIG. 24 illustrates a micro probe array device according to a third embodiment.

Referring to FIG. 24, the micro probe array device includes a working electrode 2402, an insulating layer 2403, a via contact 2404, a substrate 2405, and a reference electrode 2406. The micro probe array device includes a plurality of working electrodes 2402 (*a-c*), and the plurality of working electrodes a-c may be spaced apart by a predetermined interval, thereby enabling individual addressing. In the working electrode 2402, a tip region has a probe shape. The area of the tip area of the working electrode 2402 is set to be small in the shape of a probe, so that it is easy to invade the object 2401 such as a cell. For example, the working electrode 2402 may be configured in a conical, triangular pyramid, or square pyramid shape, but may also have a cylindrical shape.

According to an embodiment of the present invention, the substrate 2405 may be formed of a flexible material such as PDMS. When the substrate 2407 is made of a flexible material, the shape of the substrate 2407 may be changed according to an external force. As shown in FIG. 24, even if the object 2401 has a curvature, the substrate 2407 made of a flexible material may be deformed and bent according to a force applied from the outside. Then, since the micro probe array device can be in close contact with the object 2401, a uniform electrical signal can be provided to the object 2401 through the working electrode 2402.

Referring to FIG. 24, an insulating layer 2403 is disposed on an inclined surface of the working electrode 2402. The tip region of the working electrode 2402 may be not covered by the insulating layer 2403 and exposed. The tip area of the working electrode 2402 may contact the object 2401. Meanwhile, on the inclined surface of the working electrode 2402, the rest area except for the tip area may be covered by the insulating layer 2403.

The working electrode 2402 is connected to the reference electrode 2408 through a via contact 2404. A working electrode 2402 is disposed on the top of the via contact 2404, and a reference electrode 2408 is disposed on the bottom of the via contact 2404. The via contacts 2404 may be spaced apart from the substrate 104 according to a preset interval and may be disposed independently of each other. Since the via contacts 2404 are separated by the substrate 2405 made of an insulator, they are disposed to be spaced apart from each other. The tip region of the working electrode 2402 may contact the object 2401 to provide an electrical signal transmitted through the via contact 2404 to the object 2401 or obtain an electrical signal from the object 2401.

The via contact 2404 is made of a conductive material to provide a path for an electrical signal moving between the working electrode 2402 and the reference electrode 2406. The via contacts 2404 may be spaced apart from the substrate 2405 according to a preset interval and may be disposed independently of each other. Thus, the working electrodes 2402 connected to the via contact 2404 can be individually addressed without interference with each other.

The electrical signal input through the reference electrode 2406 is provided to the working electrode 2402 via a via contact 2404. The tip region of the working electrode 2402 may have a probe shape and may contact the object 2401. Thus, the electrical signal output from the working electrode 2402 is transmitted to the object 2401. Alternatively, the electric signal generated by the object 2401 may be transmitted to the working electrode 2402.

Referring to FIG. 24, the micro probe array device may further include an actuator 2407. According to an embodiment of the present invention, the height of the working electrode 2402 may be adaptively changed (increased or decreased) through external manipulation or the like. Alternatively, although the height of the working electrode 2402 is fixed, the tip region of the working electrode 2402 moves in the direction of the object 2401 according to the mechanical pressure applied by the actuator 2407 to the reference electrode 2406, and thus the degree of the contact to which the tip area of the working electrode 2402 contacts the object 2501 may increase.

The actuator 2407 may apply mechanical pressure to the reference electrode 2406.

Mechanical pressure refers to a pressure applied perpendicularly to the reference electrode 2406. The tip region of the working electrode 2402 is inserted deeper into the object 2401 according to the mechanical pressure applied by the actuator 2407 to the reference electrode 2406. The actuator 2407 may be disposed on each of the reference electrodes 2407 in the same number as the number of the reference electrodes 2406 or may be disposed only one so as to be commonly applied to the reference electrode 2406. Alternatively, one actuator 2407 may be allocated for each specific area in the micro probe array device.

The depth at which the tip region of the working electrode 2402 is inserted into the object 2401 varies according to the strength of the mechanical pressure. That is, as the mechanical pressure increases, the tip region of the working electrode 2402 is inserted deeper into the object 2401. In this case, the mechanical pressure may be adjusted based on the electric signal fed back from the object 2401.

When the strength of the electric signal fed back from the object 2401 is less than a specific reference strength, it may be determined that the contact degree between the tip region of the working electrode 2402 and the object 2401 is small. Then, as the intensity of the electric signal fed back from the object 2401 is smaller, the mechanical pressure of the actuator 2407 increases. As the mechanical pressure increases, the degree of contact between the tip area of the working electrode 2402 and the object 2401 increases. The mechanical pressure may be individually set differently for the working electrode 2402.

In FIG. 24, the insulating layer 2403 or the substrate 2405 is made of a transparent material so that the position or degree of insertion of the tip region of the working electrode 2402 into the object 2401 can be confirmed from the rear surface of the micro probe array device.

Although not shown in FIG. 24, the micro probe array device may have different heights of the working electrodes 2402 so that the working electrodes 2502 can be in close contact with the object 2501 according to the curvature of the object 2501. have. The height of the working electrode 2402 may be set differently for each area of the object 2501. The distance from the substrate 2507 to the object 2501 is determined differently for each area of the object 2501.

In addition, although not shown in FIG. 24, a counter electrode may be disposed after the working electrode 2402 and the insulating layer 2403 in the micro probe array device. In this case, the insulating layer 2403 may separate the working electrode 2402 from the counter electrode. Electrical flows may be formed between the working electrode 2402, the object 2401, and the counter electrode. For example, the electrical signal output from the working electrode 2402 may be transmitted to the object 2401 contacted by the working electrode 2402, and the electrical signal output from the object 2401 may be transmitted to the counter electrode.

Figure 25:
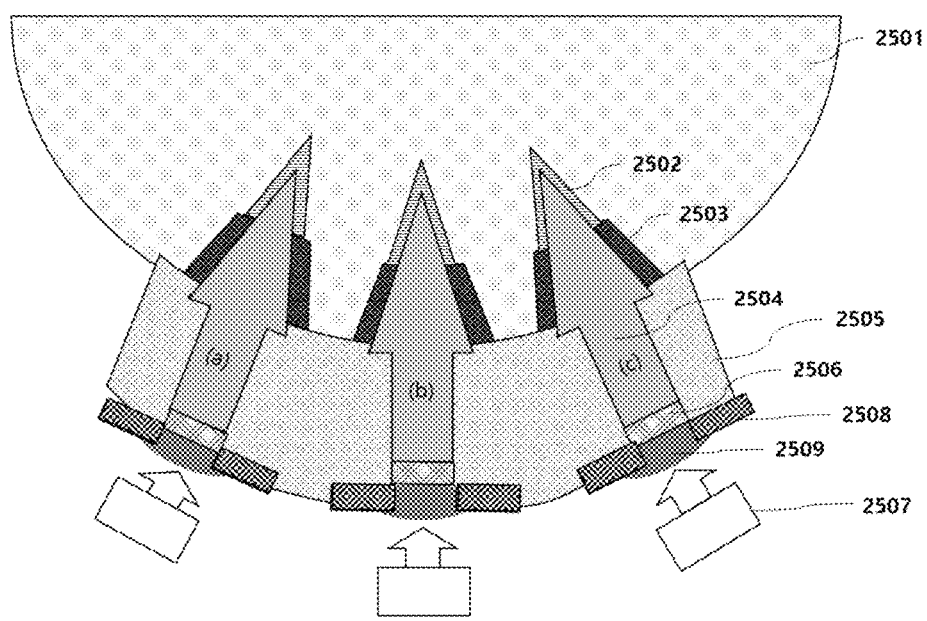
FIG. 25 illustrates a coupling relationship between a micro probe array device and a flexible PCB according to a third embodiment.

FIG. 25 illustrates a coupling relationship between a micro probe array device and a flexible PCB according to a third embodiment.

Referring to FIG. 25, a result of combining the micro probe array device shown in FIG. 24 with a flexible PCB 2506 is shown. The micro probe array device illustrated in FIG. 25 may include a working electrode 2502, an insulator 2503, a via contact 2504, a substrate 2505, and a reference electrode 2506. The flexible PCB 2508 is aligned to the reference electrode 2508 of the micro probe array device. The flexible PCB 2508 may have a hole at each position of the reference electrodes 2508 and the position between each of the reference electrodes 2508 of the micro probe array device.

After the flexible PCB 2508 and the micro probe array device are aligned, the reference electrode 2508 is connected to the conductive epoxy 2509 through a hole corresponding to the position of the reference electrode 2508 of the micro probe array device. In addition, in the flexible PCB 2508, a PDMS, which is the same flexible material as the constituent material of the substrate 2505, may be filled in a hole corresponding to a position between the reference electrodes 2508. Then, the coupling force between the flexible PCB 2508 and the micro probe array device may be improved. The conductive epoxy 2509 is connected to an external device through a connector, and the external device is a working electrode 2502, a via contact 2504, and a reference electrode 2506 of the micro probe array device implanted in the entire area of the object 2501. The electrical signal transmitted through can be measured in the external device.

FIG. 26 to 32 illustrates a method of manufacturing a probe array device according to a third embodiment.

Figure 26:
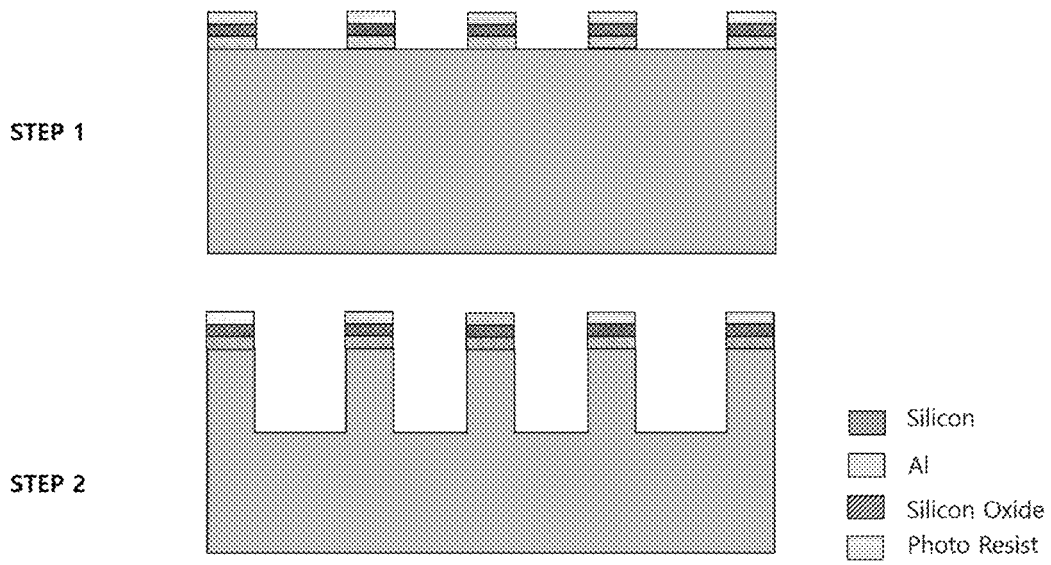
FIG. 26 to 32 illustrates a method of manufacturing a probe array device according to a third embodiment.

In STEP 1 of FIG. 26, a process of sequentially patterning aluminum, a silicon oxide layer, and a photoresist on the rear surface of the silicon wafer is performed. Specifically, a process of depositing aluminum on the rear surface of a silicon wafer, patterning a silicon oxide layer and a photoresist through photo etching, and individually patterning an aluminum electrode through aluminum wet etching is performed.

In STEP 2 of FIG. 26, a process of an anisotropic etching on the aluminum electrode patterned on the rear surface of the silicon wafer is performed for individual addressing using a mask. Anisotropic etching is performed through Deep Reactive Ion Etching (DRIE), and a plurality of silicon cylinders are formed in an array form.

Figure 27:
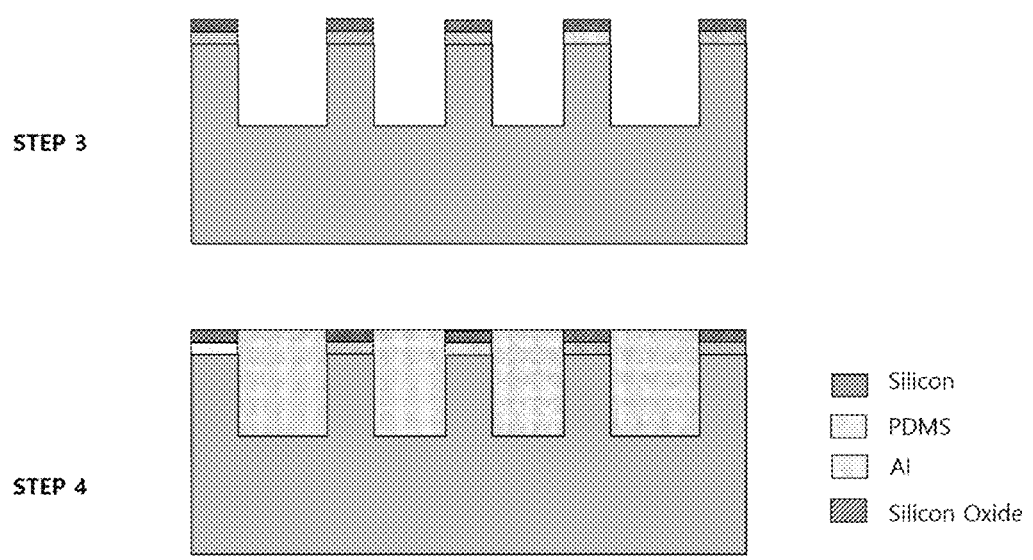

In STEP 3 of FIG. 27, a process of removing the photoresist and depositing a silicon oxide layer in the region between the silicon cylinders, and oxygen plasma treatment is performed. Through this process, the surface of the region between the silicon pillars is changed to be hydrophilic, and the adhesion between the flexible material PDMS (Polydimethylsiloxane) and the silicon may be improved In STEP 4 of FIG. 27, a process of a wet etching filling a flexible material in a region between the silicon cylinders and removing the flexible material remaining on the silicon cylinders is performed. Here, the flexible material corresponds to the substrate of the microprobe array device. The flexible material may be polydimethylsiloxane (PDMS) and may provide insulation between micro probes and flexibility of a substrate.

Figure 28:
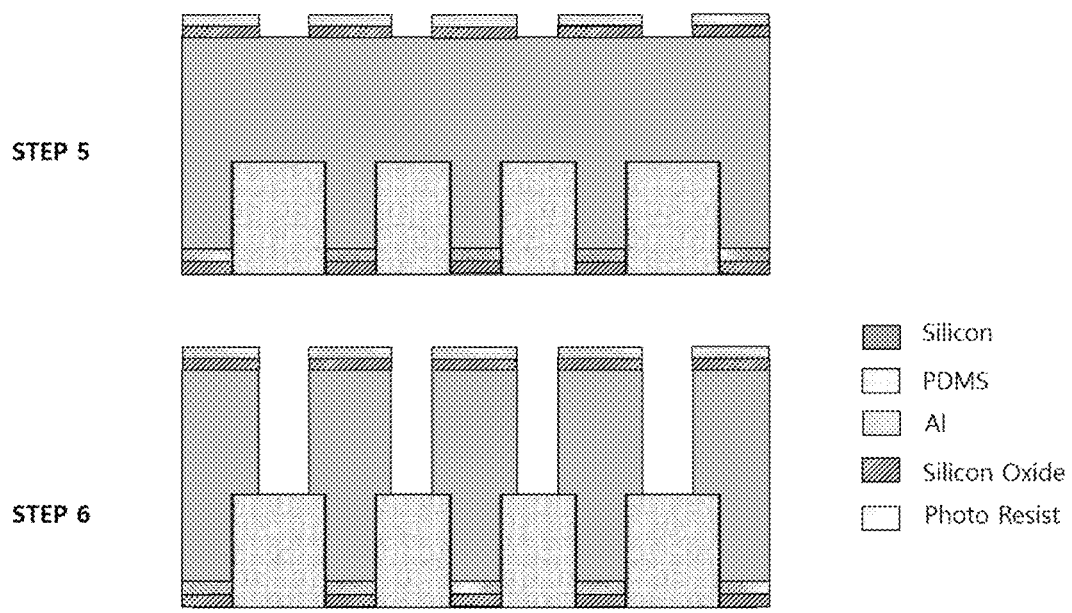

In STEP 5 of FIG. 28, a process of patterning a silicon oxide layer and a photoresist on the front surface of the silicon wafer is performed. Patterning is performed to create a silicon cylinder corresponding to the electrode of the micro probe.

In STEP 6 of FIG. 28, a process of an anisotropic etching is performed for the electrode of the micro probe. The etched depth is the depth from the front surface of the silicon wafer to the related material.

Figure 29:
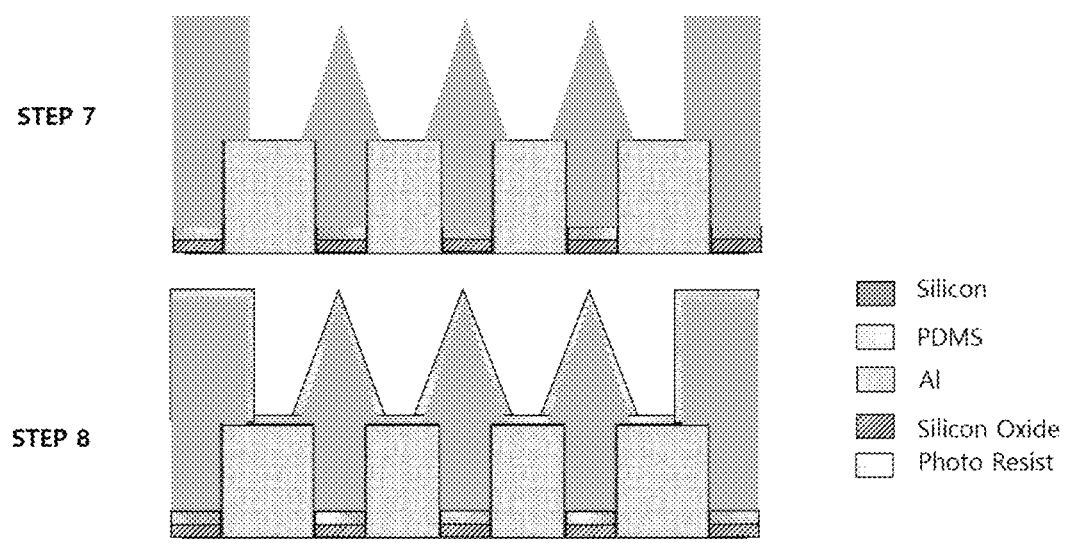

In STEP 7 of FIG. 29, a process of removing the photoresist and the oxide layer and manufacturing a micro probe based on wet etching is performed. Here, wet etching refers to isotropic wet etching using a solution in which hydrofluoric acid and nitric acid are mixed.

In STEP 8 of FIG. 29, a process of treating oxygen plasma and depositing a photoresist is performed to increase adhesion between the flexible material exposed through STEP 6 and the photoresist.

Figure 30:
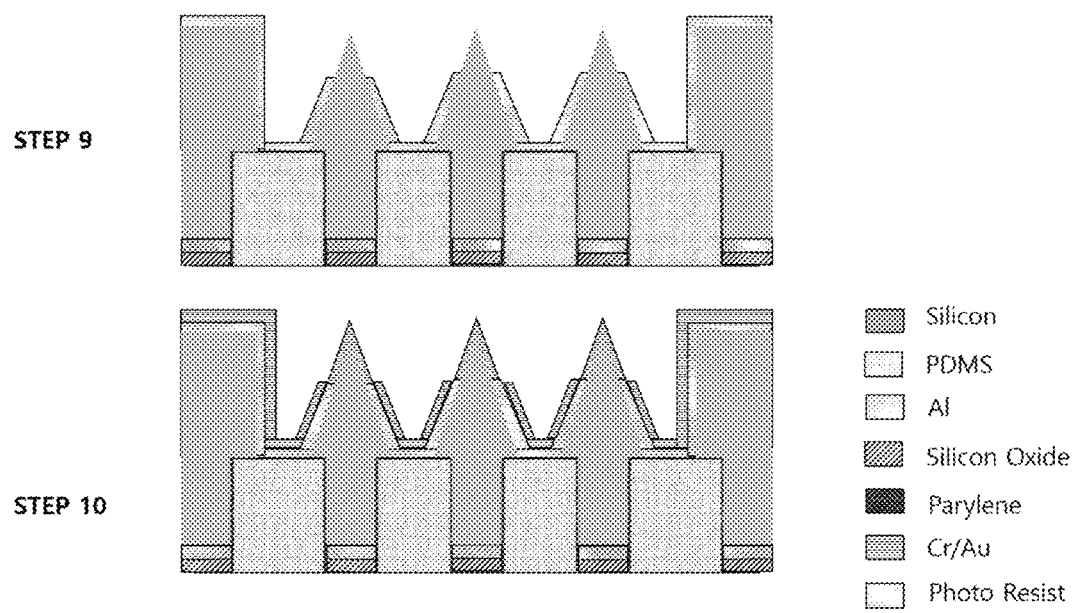

In STEP 9 of FIG. 30, a process of selectively etching the photoresist is performed through a first self-alignment process. The photoresist is etched to expose the tip area of the micro probe.

In STEP 10 of FIG. 30, a process of depositing a conductive material for generating an electrode of a micro probe is performed. Here, the conductive material may include gold or chromium.

Figure 31:
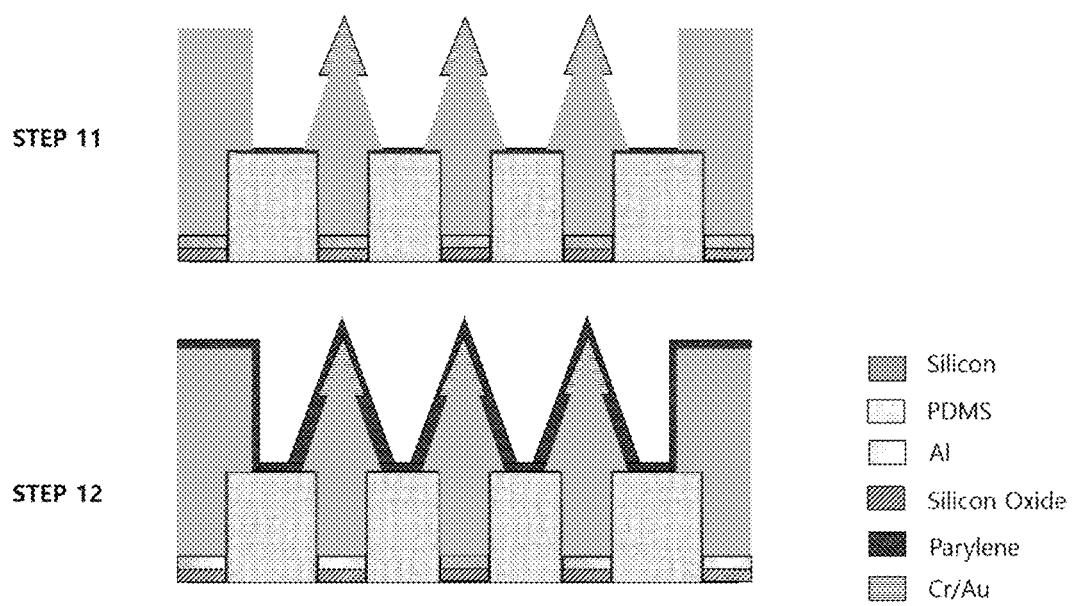

In STEP 11 of FIG. 31, a process of removing the photoresist through lift-off, and remaining the conductive material only in the tip region of the micro probe is performed. Here, the conductive material present in the tip region of the micro probe corresponds to the working electrode of the micro probe array device.

In STEP 12 of FIG. 31, a process of depositing an insulating material on the front surface of the silicon wafer is performed. Here, the insulating material may include parylene. The insulating material corresponds to the insulating layer of the microprobe array device.

Figure 32:
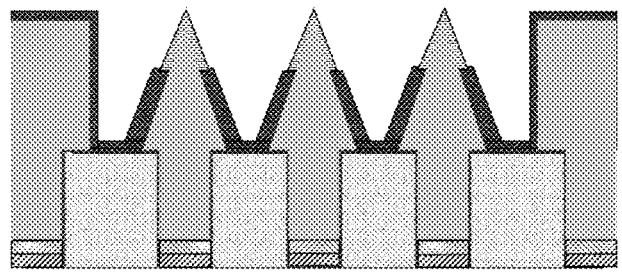
Figure 32:
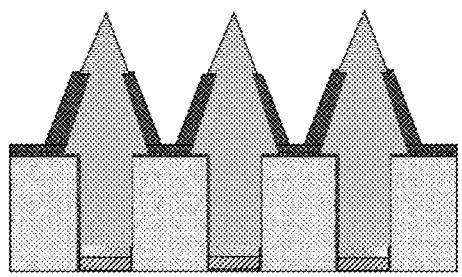

In STEP 13 of FIG. 32, a process of spin-coating a photoresist on the front surface of the silicon wafer, and an selectively etching the insulating material on the tip region of the micro probe through a second self-alignment process is performed to expose the conductive material to the outside. Accordingly, the tip region of the micro probe is exposed without being covered by the insulating material. That is, the tip region of the working electrode is exposed without being covered by the insulating layer.

In STEP 14 of FIG. 32, a process of removing and dicing the silicon oxide layer protecting the aluminum electrode on the rear surface of the silicon wafer is performed. Through this process, the micro probe array device shown in FIG. 24 is manufactured.

The present invention provides a device in which the working electrode can be inserted into the object at the same depth by arranging working electrodes of various heights in order to completely contact an object having a curvature.

The present invention provides a device capable of providing a uniform electrical signal to the entire area of an object by adaptively setting the height of a working electrode according to the curvature or shape of the object, so that it is inserted into the object at the same depth or contacted at the same level of contact. to provide.

The present invention provides a device in which a large number of micro probes are disposed in the same area by using a double electrode constituting an electric flow.

The present invention provides an apparatus that enables implantation over the entire area of an object having a curvature using an electrode of a micro probe having a flexible substrate.

The present invention provides a device capable of applying a local and selective stimulus to an object through individual addressing of working electrodes arranged in an array form.

The present invention provides a device in which the height of the electrode is changed by controlling the pressure applied to the rear surface of the micro probe through feedback of a signal measured by the electrode of the micro probe.

According to an embodiment of the present invention, there is provided a device capable of inserting the working electrode into the object at the same depth by disposing the working electrode of various heights to completely contact the object having a curvature.

According to an embodiment of the present invention, by adaptively setting the height of the working electrode according to the curvature or shape of the object, it is inserted into the object at the same depth or contacted with the same degree of contact to provide a uniform electrical signal to the entire area of the object.

According to an embodiment of the present invention, a device capable of applying a local and selective stimulus to an object through individual addressing of working electrodes arranged in an array form is provided.

According to an embodiment of the present invention, fine probes having a high aspect ratio may be provided by using silicon anisotropic etching.

According to an exemplary embodiment of the present invention, a different stimulus may be applied to each area of an object by individually addressing the fine probes using a silicon anisotropic etching process and a glass reflow process.

According to an embodiment of the present invention, since a micro probe array device can be provided with a small number of masks by using a self-alignment process, a micro probe array device having a double electrode having a complex structure can be manufactured through an inexpensive and simple process.

According to an embodiment of the present invention, it is possible to manufacture a micro-probe array device in which a working electrode and a counter electrode are integrated in a double electrode form, so that a larger number of micro-probes can be placed in the same area, thereby realizing more pixels.

According to an embodiment of the present invention, a signal of a specific part can be viewed, and different stimuli can be applied to an object by enabling the micro probes to be individually addressed.

According to an exemplary embodiment of the present invention, the substrate is made of a flexible material so that the micro-probe array device can be implanted on the entire area of an object such as a nerve or cell having a curvature.

According to an exemplary embodiment of the present invention, the electrode region is exposed only at the tip of the fine probe, thereby reducing noise.

According to an embodiment of the present invention, the height of the electrode is changed by adjusting the pressure applied to the rear surface of the micro probe through feedback of a signal measured by the electrode of the micro probe, so that a uniform electric signal can be provided to the object.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents.

What is claimed is:

1. A micro probe array device, comprising:
a substrate;
a via contact formed through the substrate;
a working electrode in the form of a probe formed on an upper end of the via contact;
a reference electrode formed at a lower end of the via contact and is configured to provide an electric signal flowing through the via contact to the working electrode;
an insulating layer formed on a portion of the working electrode,
wherein the working electrode is arranged in an array form, and at least one working electrode having different heights is included in the micro probe array device, and
a counter electrode disposed on the insulating layer which separates an electrical connection between the counter electrode and the working electrode in manner that when the working electrode and the counter electrode both are in contact with an object, electrical signal flows from the working electrode to the object and flows from the object to the counter electrode.

2. The micro probe array device of claim 1, wherein a tip region of the working electrode is not covered by the insulating layer and is exposed to the outside, and a remain area except for the tip area of the working electrode is covered by the insulating layer.

3. The micro probe array device of claim 1, the height of the working electrode is set differently according to the distance between the substrate and the object contacting the tip region of the working electrode, wherein the distance is determined according to the shape or curvature of the object.

4. The micro probe array device of claim 1, wherein the working electrode is connected to the reference electrode through a via contact, and wherein the via contacts are spaced apart from each other according to a predetermined distance in the substrate and are disposed independently of each other in the substrate.

5. The micro probe array device of claim 1, wherein the tip region of the working electrode is configured to contact with the object and provide an electric signal transmitted through the via contact to the object or to obtain an electric signal transmitted from the object.

6. The micro probe array device of claim 1, wherein the height of the working electrode is adjusted corresponding to the curvature of the object.

7. The micro probe array device of claim 1, wherein a distance between the working electrode and the object becomes closer or a depth to be inserted into the object increases, when a mechanical pressure of an actuator is applied to the reference electrode.

8. The micro probe array device of claim 1, wherein mechanical pressure is determined based on the electrical signal being fed back from the object.

9. The micro probe array device of claim 8, wherein the mechanical pressure increases, when the electric signal fed back from the object is less than or equal to a predetermined strength.

10. The micro probe array device of claim 1, wherein the substrate is formed of a fixed material that is not deformed by external pressure or a flexible material that is deformed by external pressure.

11. A micro probe array device, comprising:
a substrate;
a via contact formed through the substrate;
a working electrode in the form of a probe formed on an upper end of the via contact;
a reference electrode formed at a lower end of the via contact and is configured to provide an electric signal flowing through the via contact to the working electrode;
a first insulating layer formed on the working electrode;
a counter electrode formed on the first insulating layer;
a second insulating layer formed on the counter electrode, wherein a flow of the electrical signal between the working electrode, the counter electrode, and objects in contact with the working electrode, and
the counter electrode is disposed on the first insulating layer which separates an electrical connection between the counter electrode and the working electrode in manner that when the working electrode and the counter electrode both are in contact with an object, electrical signal flows from the working electrode to the object and flows from the object to the counter electrode.

12. The micro probe array device of claim 11, wherein a tip region of the working electrode is not covered by the first insulating layer and is exposed to the outside, and a remain area except for the tip area of the working electrode is covered by the first insulating layer.

13. The micro probe array device of claim 11, wherein a length of the working electrode is different from a length of the counter electrode.

14. The micro probe array device of claim 13, wherein the length of the working electrode is longer than the length of the counter electrode.

15. The micro probe array device of claim 11, the height of the working electrode is set differently according to the distance between the substrate and the objects contacting the tip region of the working electrode,
wherein the distance is determined according to the shape or curvature of the object.

16. The micro probe array device of claim 11, wherein the working electrode is connected to the reference electrode through a via contact, and wherein the via contacts are spaced apart from each other according to a predetermined distance in the substrate and are disposed independently of each other in the substrate.

17. The micro probe array device of claim 11, wherein the tip region of the working electrode is configured to contact with the object and provide an electric signal transmitted through the via contact to the object or to obtain an electric signal transmitted from the object.

18. The micro probe array device of claim 11, wherein the height of the working electrode is adjusted corresponding to the curvature of the object.

19. The micro probe array device of claim 11, wherein a distance between the working electrode and the object becomes closer or a depth to be inserted into the object increases, when a mechanical pressure of an actuator is applied to the reference electrode.

20. The micro probe array device of claim 19, wherein the mechanical pressure is determined based on the electrical signal being fed back from the object.

21. The micro probe array device of claim 20, wherein the mechanical pressure increases, when the electric signal fed back from the object is less than or equal to a predetermined strength.

22. The micro probe array device of claim 11, wherein a specific region of the counter electrode is not covered by the second insulating layer and is exposed to the outside, and a remain area except for the specific area of the counter electrode is covered by the second insulating layer.

23. The micro probe array device of claim 11, wherein the working electrodes that are adjacent to each other are formed to be spaced apart from each other, and wherein the counter electrodes that are adjacent to each other are formed to be connected to each other or formed to be spaced apart from each other.

24. The micro probe array device of claim 11, wherein the substrate is formed of a fixed material that is not deformed by external pressure or a flexible material that is deformed by external pressure.

25. A micro probe array device, comprising:
a substrate;
a via contact formed through the substrate;
a working electrode in the form of a probe formed on an upper end of the via contact;
a reference electrode formed at a lower end of the via contact and is configured to provide an electric signal flowing through the via contact to the working electrode;
an insulating layer formed on a portion of the working electrode,
wherein the substrate is composed of a flexible material that can be bent by external pressure to correspond to the curvature of an object, and
a counter electrode disposed on first insulating layer which separates an electrical connection between the counter electrode and the working electrode in manner that when the working electrode and the counter electrode both are in contact with the object, electrical signal flows from the working electrode to the object and flows from the object to the counter electrode.

26. The micro probe array device of claim 25, wherein a tip region of the working electrode is not covered by the insulating layer and is exposed to the outside, and a remain area except for the tip area of the working electrode is covered by the insulating layer.

27. The micro probe array device of claim 25, the height of the working electrode is set differently according to the distance between the substrate and the objects contacting the tip region of the working electrode,
wherein the distance is determined according to the shape or curvature of the object.

28. The micro probe array device of claim 25, wherein the working electrode is connected to the reference electrode through a via contact, and wherein the via contacts are spaced apart from each other according to a predetermined distance in the substrate and are disposed independently of each other in the substrate.

29. The micro probe array device of claim 25 further comprising a flexible PCB is coupled to the lower end of the micro probe array device, wherein a hole of the flexible PCB is formed at a position of the reference electrode of the micro probe array device and is coupled to the micro probe array device through a conductive epoxy.

30. The micro probe array device of claim 25, wherein the tip region of the working electrode is configured to contact with the object and provide an electric signal transmitted through the via contact to the object or to obtain an electric signal transmitted from the object.

31. The micro probe array device of claim 25, wherein the height of the working electrode is adjusted corresponding to the curvature of the object.

32. The micro probe array device of claim 25, wherein a distance between the working electrode and the object becomes closer or a depth to be inserted into the object increases, when a mechanical pressure of an actuator is applied to the reference electrode.

33. The micro probe array device of claim 32, wherein the mechanical pressure is determined based on the electrical signal being fed back from the object.

34. The micro probe array device of claim 33, wherein the mechanical pressure increases, when the electric signal fed back from the object is less than or equal to a predetermined strength.

35. The micro probe array device of claim 25, wherein the substrate is formed of a fixed material that is not deformed by external pressure or a flexible material that is deformed by external pressure.

\* \* \* \* \*